US007504377B2

(12) United States Patent
Tye

(10) Patent No.: US 7,504,377 B2
(45) Date of Patent: Mar. 17, 2009

(54) NITRIC OXIDE-BLOCKED CROSS-LINKED TETRAMERIC HEMOGLOBIN

(75) Inventor: Ross Walden Tye, Chico, CA (US)

(73) Assignee: IKOR, Inc., Aberdeen, SD (US)

( * ) Notice: Subject to any disclaimer, the term of this patent is extended or adjusted under 35 U.S.C. 154(b) by 0 days.

(21) Appl. No.: 11/713,195

(22) Filed: Mar. 1, 2007

(65) Prior Publication Data

US 2008/0096805 A1    Apr. 24, 2008

Related U.S. Application Data

(63) Continuation-in-part of application No. 11/586,312, filed on Oct. 24, 2006.

(60) Provisional application No. 60/853,968, filed on Oct. 23, 2006.

(51) Int. Cl.
*C07K 14/00* (2006.01)
(52) U.S. Cl. .......................................... 514/6; 530/385
(58) Field of Classification Search ........................ None
See application file for complete search history.

(56) References Cited

U.S. PATENT DOCUMENTS

| | | | |
|---|---|---|---|
| 4,473,494 A | 9/1984 | Tye |
| 4,529,719 A | 7/1985 | Tye |
| 4,650,786 A | 3/1987 | Wong |
| 4,670,417 A | 6/1987 | Iwasaki et al. |
| 4,727,027 A | 2/1988 | Wiesehahn et al. |
| 5,028,588 A | 7/1991 | Hoffman et al. |
| 5,084,558 A | 1/1992 | Rausch et al. |
| 5,189,146 A | 2/1993 | Hsia |
| 5,234,903 A | 8/1993 | Nho et al. |
| 5,281,579 A | 1/1994 | Estep |
| 5,290,919 A | 3/1994 | Bucci et al. |
| 5,352,773 A | 10/1994 | Kandler et al. |
| 5,380,824 A | 1/1995 | Marschall et al. |
| 5,386,014 A | 1/1995 | Nho et al. |
| 5,532,352 A | 7/1996 | Pliura et al. |
| 5,563,047 A | 10/1996 | Petersen |
| 5,599,907 A | 2/1997 | Anderson et al. |
| 5,627,266 A | 5/1997 | Wainwright et al. |
| 5,733,869 A | 3/1998 | Burhop et al. |
| 5,747,663 A | 5/1998 | Coplan et al. |
| 5,750,132 A | 5/1998 | Gerber |
| 5,753,616 A | 5/1998 | Rausch et al. |
| 5,776,890 A | 7/1998 | Hoffman et al. |
| 5,789,376 A | 8/1998 | Hsia |
| 5,811,005 A | 9/1998 | Hsia |
| 5,840,701 A | 11/1998 | Hsia |
| 5,844,090 A | 12/1998 | Anderson et al. |
| 5,929,031 A | 7/1999 | Kerwin et al. |
| 6,894,150 B1 | 5/2005 | Tye |
| 7,019,117 B2 | 3/2006 | Acharya et al. |
| 2008/0096803 A1 | 4/2008 | Tye |

FOREIGN PATENT DOCUMENTS

| | | |
|---|---|---|
| WO | WO 90/13645 A1 | 11/1990 |
| WO | WO 92/02239 A1 | 2/1992 |
| WO | WO 92/08478 A1 | 5/1992 |
| WO | WO 92/11283 A1 | 7/1992 |
| WO | WO 92/22646 A1 | 12/1992 |
| WO | WO 94/26286 A1 | 11/1994 |

OTHER PUBLICATIONS

Allison, et al. The bioassay of human endogenous pyrogen. Clin Sci Mol Med. 1973; 45(4):449-58.
Benesch, et al. Affinity labeling of the polyphosphate binding site of hemoglobin. Biochemistry. 1972; 11(19):3576-82.
Benesch, et al. Hemoglobin covalently bridged across the polyphoshate binding site. Biochem Biophys Res Commun. 1975; 63(4):1123-9.
Benesch, et al. Labeling of hemoglobin with pyridoxal phosphate. J. Bio. Chem. 1982; 257(3):1320-1324.
Benesch, et al. Preparation and properties of hemoglobin modified with derivatives of pyridoxal. Methods Enzymol. 1981; 76:147-59.
Bleeker, et al. Endotoxin in blood products: correlation between the Limulus assay and the rabbit pyrogen test. Prog Clin Biol Res. 1985;189:293-303.
Chan, et al. Slow phase hemolysis in hypotonic electrolyte solutions. J Cell Physiol. 1975; 85(1):47-57.
Dietz, et al. The effects of cross linked hemoglobin on regional vascular conductance in dogs. Anesth Analg 1997; 85: 265-273.
Dolman, et al. Membrane-covered thin-layer optical cell for gas-reaction studies of hemoglobin. Anal Biochem. 1978; 87(1):127-34.
Eperon, et al. Human monocytoid cell lines as indicators of endotoxin: comparison with rabbit pyrogen and Limulus amoebocyte lysate assay. J Immunol Methods. 1997; 207(2):135-45.
Faivre-Fiorina, et al. Presence of hemoglobin inside aortic endothelial cells after cell-free hemoglobin administration in guinea pig. Am J Physiol Heart Circ Physiol 1999; 276: H766-H770.

(Continued)

*Primary Examiner*—Karen Cochrane Carlson
(74) *Attorney, Agent, or Firm*—Albert P. Halluin; Peggy A. Radel; Wilson Sonsini Goodrich & Rosati

(57) ABSTRACT

The present invention includes compositions containing carboxamidomethylated cross-linked hemoglobin where the cysteine moiety of the hemoglobin includes a thiol protecting group and where the hemoglobin has a reduced ability to bind with nitric oxide. Preferably, the hemoglobin is deoxygenated, endotoxin free, and stroma free. The present invention also includes method of preparation, process of preparation and the method of use including supplementing blood volume in mammals and treating disorders in mammals where oxygen delivery agents are of benefit.

43 Claims, 11 Drawing Sheets
(3 of 11 Drawing Sheet(s) Filed in Color)

OTHER PUBLICATIONS

Friedman, et al. Morphologic effects following massive exchange transfusions with a stroma-free hemoglobin solution. I. Liver. Lab Invest. 1978; 39(2):167-77.

Fujiwara, et al. Measurement of endotoxin in blood products using an endotoxin-specific Limulus test reagent and its relation to pyrogenic activities in rabbit. Yakugaku Zasshi. 1990; 110(5):332-40. (in Japanese with English abstract).

Gulati, et al. Effect of diaspirin crosslinked and stroma-reduced hemoglobin on mean arterial pressure and endothelin-1 concentration in rats. Life. Sci 1995; 56:1433-1442.

Gulati, et al. Role of adrenergic mechanisms in the pressor effect of diaspirin cross-linked hemoglobin. J Lab Clin Med 1994; 124: 125-33. (Abstract only. 1 page.).

Gulati, et al. Role of endothelin in the cardiovascular effects of diaspirin crosslinked and stroma reduced hemoglobin. Crit. Care Med 1996; 24: 137-47. (21 pages).

Hale, A. S. Canine blood groups and their importance in veterinary transfusion medicine. Vet Clin North Am Small Anim Pract. 1995; 25(6):1323-32.

Harrell, et al. Canine transfusion reactions and their management. Vet Clin North Am Small Anim Pract. 1995; 25(6):1333-64.

Intaglietta, et al. Microvascular and tissue oxygen distribution. Cardiovasc Res 1996; 32: 632-43.

Jia, et al. S-nitrosohaemoglobin: a dynamic activity of blood involved in vascular control. Nature. 1996; 380(6571):221-6.

Kasper, et al. Effects of a hemoglobin-based oxygen carrier (HBOC-201) on hemodynamics and oxygen transport in patients undergoing preoperative hemodilution for elective abdominal aortic surgery. Anesth Analg 1996; 83: 921-7.

Kasper, et al. The effects of increased doses of bovine hemoglobin on hemodynamics and oxygen transport in patients undergoing preoperative hemodilution for elective abdominal aortic surgery. Anesth Analg 1998; 87: 284-91.

Katsuyama, et al. Nitric oxide mediates the hypertensive response to a modified hemoglobin solution (DCLHb) in rats. Artif Cells Blood Substit Immobil Biotechnol. 1994; 22(1):1-7.

Lawn, et al. The nucleotide sequence of the human beta-globin gene. Cell. 1980; 21(3):647-51.

Levy, et al. Polymerized bovine hemoglobin solution as a replacement for allogeneic red blood cell transfusion after cardiac surgery: results of a randomized, double-blind trial. J Thorac Cardiovasc Surg 2002; 124: 35-42.

Liebhaber, et al. Cloning and complete nucleotide sequence of human 5'-alpha-globin gene. Proc Natl Acad Sci U S A. 1980; 77(12):7054-8.

MacDonald, et al. Coronary vasoconstrictor activity of purified and modified human hemoglobin. Biomater Artif Cells Artif Organs 1990; 18: 263-282.

Marotta, et al. Human beta-globin messenger RNA. III. Nucleotide sequences derived from complementary DNA. J Biol Chem. 1977; 252(14):5040-53.

Martel, et al. Limulus test using a chromogenic method: application to the control of pyrogens in blood derivatives. Rev Fr Transfus Immunohematol. 1985; 28(3):237-50. (in French with English summary).

McCarthy, et al. The role of facilitated diffusion in oxygen transport by cell-free hemoglobins: implications for the design of hemoglobin-based oxygen carriers. Biophys Chem 2001; 92: 103-17. (Abstract only. 1 page.).

Pool, et al. The detection of pyrogens in blood products using an ex vivo whole blood culture assay. J Immunoassay. 1998; 19(2-3):95-111.

Poole, et al. Assay of pyrogenic contamination in pharmaceuticals by cytokine release from monocytes. Dev Biol Stand. 1988; 69:121-3.

Rabiner, et al. Evaluation of a stroma-free hemoglobin solution for use as a plasma expander. J Exp Med. 1967; 126(6):1127-42.

Sakai, et al. Microvascular responses to hemodilution with Hb vesicles as red blood cell substitutes: influence of O2 affinity. Am J Physiol. Feb. 1999;276(2 Pt 2):H553-62.

Sakai, et al. Molecular dimensions of Hb-based O2 carriers determine constriction of resistance arteries and hypertension. Am J Physiol 2000; 279: H908-H915.

Schechter, et al. Hemoglobin and the paracrine and endocrine functions of nitric oxide. N Engl J Med 2003; 348: 1483-5.

Schnackerz, et al. Specific receptor sites for pyridoxal 5'-phosphate and pyridoxal 5'-deoxymethylenephosphonate at the alpha and beta NH2-terminal regions of hemoglobin. J Biol Chem. 1983; 258(2):872-5.

Schultz, et al. A role for endothelin and nitric oxide in the pressor response to diaspirin cross-linked hemoglobin. J Lab Clin Med. 1993; 122(3):301-8.

Schwarz, et al. The use of a hollow fiber membrane module in sample conditioning prior to electrophoresis. Electrophoresis. 1994; 15(8-9):1118-9.

Simon, et al. Studies of the sensitivity and reproducibility of pharmacopoeial pyrogen testing. Dev Biol Stand. 1977; 34:75-84.

Spahn, et al. Cardiovascular and coronary physiology of acute isovolemic hemodilution: a review of nonoxygen-carrying and oxygen-carrying solutions. Anesth Analg 1994; 78: 1000-21.

Spahn, et al. Physiological properties of blood substitutes. News Physiol Sci 2001; 16: 38-41.

Stowell, et al. Progress in the development of RBC substitutes. Transfusion 2001; 41: 287-99.

Taktak, et al. Assay of pyrogens by interleukin-6 release from monocytic cell lines. J Pharm Pharmacol. 1991; 43(8):578-82.

Vandegriff, et al. MP4, a new nonvasoactive PEG-Hb conjugate. Transfusion. 2003; 43: 509-16.

Winslow, R. M. Current status of blood substitute research: towards a new paradigm. J Intern Med 2003; 253: 508-17.

Cheng et al. Ligand binding properties and structural studies of recombinant and chemically modified hemoglobins altered at beta 93 cysteine. Biochemistry. Oct. 1, 2002;41(39):11901-13.

Cohn. The current status of haemoglobin-based blood substitutes. Ann Med. Oct. 1997;29(5):371-6.

De Venuto, et al. Total and partial blood exchange in the rat with hemoglobin prepared by crystallization. Transfusion. Nov.-Dec. 1977;17(6):555-6.

Didonato et al. Selective carboxymethylation of the alpha-amino groups of hemoglobin. Effect on functional properties. J Biol Chem. Oct. 10, 1983;258(19):11890-5.

Eaton. Hemoglobin-based blood substitutes: A dream-like trade of blood and guile? J. Lab Clin. Med. 1996; 127(5):416-417.

Fantl et al. Properties of carboxymethylated cross-linked hemoglobin A. Biochemistry. Sep. 8, 1987;26(18):5755-61.

Guidotti. The rates of reaction of the sulfhydryl groups of human hemoglobin. J Biol Chem. Oct. 1965;240(10):3924-7.

Jones. Red Blood Cell Substitutes: Current Status. Br. J. Anaesth. 1995; 74: 697-703.

Kroeger et al. Structures of Hemoglobin-based Blood Substitute: Insights into the Function of Allosteric Proteins. Structure. 1997; 5(2): 227-37.

Langermans et al. Safety evaluation of a polymerized hemoglobin solution in a murine infection model. J. Lab. Clin Med. 1996; 127(5): 428-34.

Lieberthal. Storma-free hemoglobin: A potential blood substitute. J. Lab. Clin Med. 1995; 126:231-2.

Manning et al. Influence of ligation state and concentration of hemoglobin A on its cross-linking by glycolaldehyde: functional properties of cross-linked, carboxymethylated hemoglobin. Biochemistry. Aug. 23, 1988;27(17):6640-4.

Manning. Preparation of hemoglobin carbamylated at specific NH2-terminal residues. Methods Enzymol. 1981;76:159-67.

Ogden et al. Haemoglobin-Based Red Cell Substitutes: Current Status. Vox Sang. 1995; 69:302-308.

Schreiber, et al. The risk of transfusion-transmitted viral infections. N Engl J Med No. 26 (1996);334: 1685-90.

Taylor et al. Studies on human hemoglobin treated with various sulfhydryl reagents. J Biol Chem. Jan. 10, 1966;241(1):241-8.

Winslow. Blood Substitutes. Science & Medicine. 1996; 4(2): 54-63.

Tye, R. W. U.S. Appl. No. 11/586,312, entitled "Carboxymethylated cross-linked tetrameric hemoglobin," filed on Oct. 24, 2006.

International communication dated Jul. 18, 2008 from PCT Application No. US07/80337.

Standards Run for Size Calibrations

Overlay of Electrophoretic Separations of Native and Crosslinked Hemoglobin Plotted Against Size Standard (Expanded View)

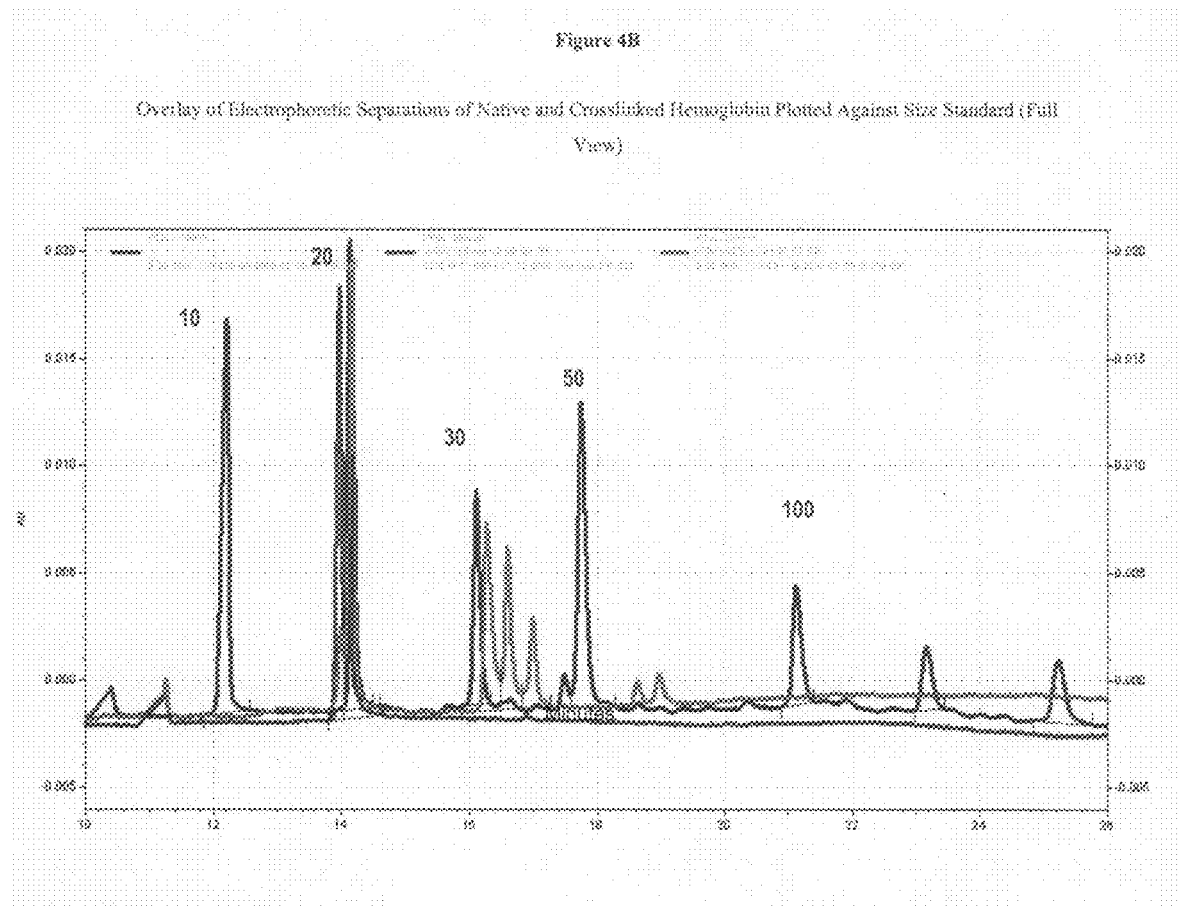

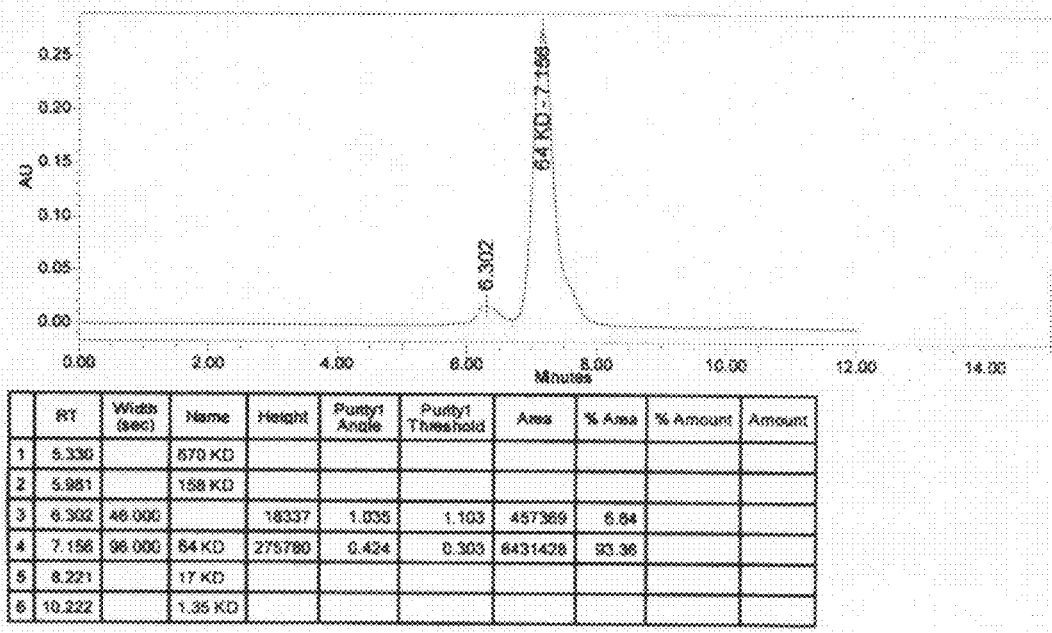

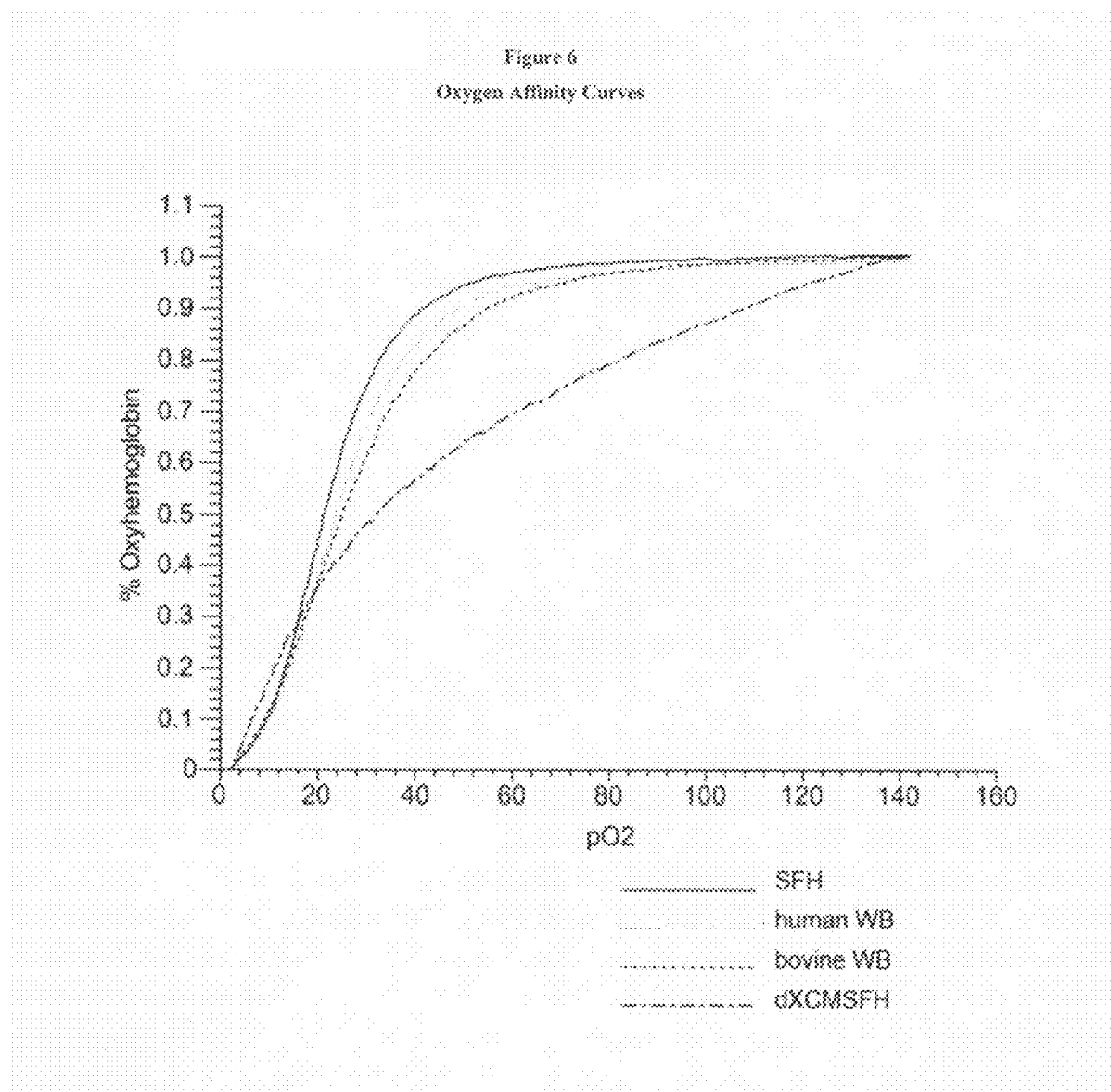

NITRIC OXIDE-BLOCKED CROSS-LINKED TETRAMERIC HEMOGLOBIN

This application is a continuation-in-part application of application Ser. No. 11/586,312, filed Oct. 24, 2006 which claims the benefit of U.S. Provisional Application Ser. No. 60/853,968, filed Oct. 23, 2006.

INTRODUCTION

This invention relates to nitric oxide-blocked cross linked tetrameric hemoglobins, more specifically to a carboxamidomethylated cross linked tetrameric hemoglobin, which has low reactivity with nitric oxide (NO), and which is cross linked to stabilize the tetramer for in-vivo applications. Methods of preparation and use as blood volume expansion agents and as oxygen delivery therapy agents are also disclosed.

BACKGROUND OF THE INVENTION

One of the limitations on the use of blood in an emergency setting is a requirement to type and cross-match the blood to minimize the risk of transfusion reactions. Type and cross-matching may require at least 10 minutes and a complete type and cross-match can take up to an hour. Furthermore, the risk of HIV transmission has been estimated to be 1 in 500,000 units of blood and the risk of hepatitis C transmission has been estimated to be 1 in 3,000 units. The safety of blood supply and blood logistics are critical issues in developing countries, where the risk of infectious disease transmission as well as the risk of outdated supply is relatively higher. Up to 25% of the blood is discarded in developing countries because of the presence of infectious disease. Hence, there are pressing factors to find blood substitutes or artificial blood compositions that avoid disease transmission and provide rapid response to improve chances of survival.

Two aspects of artificial blood use in clinical settings are volume expansion and oxygen therapeutics. Volume expander agents are inert, merely increasing, blood volume, and thus allow the heart to pump fluid efficiently. Oxygen therapeutics mimic human blood's oxygen transport ability. Oxygen therapeutics can be divided in two categories based on transport mechanism: perfluorocarbon based, which function by simple dissolution of oxygen, and hemoglobin protein based, which transports oxygen by facilitated capture and release. In hemoglobin-based products, pure hemoglobin (Hb) separated from red blood cells (RBCs) may not be useful for a number of reasons, including instability, induction of renal toxicity, and unsuitable oxygen transport and delivery characteristics when separated from red blood cells.

Hemoglobin based oxygen therapeutics have been shown to exert various degrees of vasoactive effects both in animal and human studies (Winslow et al., *Adv Drug Del Rev* 2000; 40: 131-42;Stowell et al., *Transfusion* 2001; 41: 287-99; Spahn et al., *News Physiol Sci* 2001; 16: 38-41; Spahn et al., *Anesth Analg* 1994; 78: 1000-21; Kasper et al., *Anesth Analg* 1996; 83: 921-7; Kasper et al., *Anesth Analg* 1998; 87: 284-91; Levy et al., *J Thorac Cardiovasc Surg* 2002; 124: 35-42;). This vasoactivity may be due to the effects of these products in binding intracellular NO (Kasper et al., *Anesth Analg* 1996; 83: 921-7; Dietz et al., *Anesth Analg* 1997; 85: 265-273; Schechter et al., *N Engl J Med* 2003; 348: 1483-5), endothelial release (Gulati et al., *Crit. Care Med* 1996; 24: 137-47), or sensitization of peripheral α-adrenergic receptors (Gulati et al., *J Lab Clin Med* 1994; 124: 125-33). Alternatively, the increased vasoconstrictive effects could be due to increases in the rate of oxygen release, secondary to the administration of these products, at a higher concentration than RBCs, resulting in vasoconstriction (Winslow et al., *J Intern Med* 2003; 253: 508-17; McCarthy et al., *Biophys Chem* 2001; 92: 103-17; Intaglietta et al., *Cardiovasc Res* 1996; 32: 632-43; Vandegriff et al., *Transfusion* 2003; 43: 509-16).

The ability of stroma-free Hb solutions to induce blood pressure increases has been known. It has been demonstrated that some cross-linked Hb solutions could increase mean arterial pressure as much as 25-30% in a dose-dependent manner within 15 min of administration and that the effect could last as long as 5 h.

Vasoconstriction may be due to NO scavenging by the hemoglobin based therapeutic (Katsuyama et al., *Artif Cells Blood Substit Immobil Biotechnol* 1994;22:1-7; Schultz et al., *J Lab Clin Med* 1993; 122:301-308, hereby incorporated by reference in its entirety). Vasoconstriction could be also caused by the contamination of the hemoglobin by phospholipids and endotoxin. Although the remaining phospholipids and endotoxin contamination during Hb purification may cause hemodynamic effects (Macdonald et al., *Biomater Artif Cells Artif Organs* 1990; 18: 263-282), it is less likely that this contamination be the major factor explaining the potent vasoactive effect of some of these products (Gulati et al., *Life Sci* 1995; 56: 1433-1442).

NO is a smooth-muscle relaxant that functions via activation of guanylate cyclase and the production of cGMP or by direct activation of calcium-dependent potassium channels. The increase in the free Hb can result in an increase in the NO binding. The increase in the NO binding can result in transient and in repeat dosing, sustained hemodynamic changes responding to vasoactive substances or the lack of vasoactive regulatory substances. In some circumstances the lack of nitric oxide may lead to blood pressure increases and if prolonged, hypertension. It has been demonstrated that NO may bind to the reactive sulfhydryls of Hb and may be transported to and from the tissues in a manner analogous to the transport of oxygen by heme groups (Jia et al., *Nature* 1996; 80:221-226).

Nitric oxide along with precapillary sphincter movement are regulators of the arteriolar perfusion of any tissue. Nitric oxide is synthesized and released by the endothelium in the arterial wall, where it can be bound by hemoglobin in red blood cells. When a tissue is receiving high levels of oxygen, nitric oxide is not released and the arterial wall muscle contracts making the vessel diameter smaller, thus decreasing perfusion rate and cause a change in cardiac output. When demand for oxygen increases, the endothelium releases nitric oxide, which causes vasodilatation. The nitric oxide control of arterial perfusion operates over the distance that NO diffuses after release from the endothelium. Nitric oxide is also needed to mediate certain inflammatory responses. For example, nitric oxide produced by the endothelium inhibits platelet aggregation. Consequently, as nitric oxide is bound by cell-free hemoglobin, platelet aggregation may be increased. As platelets aggregate, they release potent vasoconstrictor compounds such as thromboxane $A_2$ and serotonin. These compounds may act synergistically with the reduced nitric oxide levels caused by hemoglobin scavenging resulting in significant vasoconstriction. In addition to inhibiting platelet aggregation, nitric oxide also inhibits neutrophil attachment to cell walls, which in turn may lead to cell wall damage. Because nitric oxide binds to hemoglobin inside the red blood cell, it is expected that nitric oxide may bind to free Hb (stroma free crosslinked tetrameric Hb) as well.

In many formulations free Hb and stabilized hemoglobin infusions appear to be linked to vasoconstriction of the blood vessels, resulting in extremely high blood pressures. The hemoglobin moiety of these products can diffuse into the endothelial lining of the vascular wall and act as a sink in binding and removing NO which is needed for maintaining the normal tone of the vascular wall. This can result in vasoconstriction of the smooth muscle cells of the vascular wall. The free Hb solution can leak into the surrounding tissues. Also, the extent of vasoconstriction which occurs subsequent to administration of different molecular size hemoglobin-based therapeutic bears an inverse relationship to the molecular size of the product used, i.e. infusion of larger oxygen carriers results in less vasoconstriction and hypertension (Sakai, et al. *Am J Physiol* 2000; 279: H908-15). The smaller sized Hb molecule may be the most permeable and may show a higher level of vasoconstriction and hypertension (Faivre-Fiorina et al., *Am J Physiol Heart Circ Physiol* 1999; 276: H766-70). In rabbit models, transfusion of free Hb through the ear vein has caused cerebral vasculature ischemia and death. Therefore, it is important to minimize the impact of administration of most free Hb on the arterial system during administration. Vasoactive agents such as verapamil, atenocard, sildenafil citrate, etc., may be administered to the patient prior to free Hb infusion. This is intended to ensure that the arterial system is minimally changed during infusion. Nitric oxide and verapamil are preferred vasoactive agents. Slow channel calcium blockers (or a selective inhibitor of cyclic guanosine monophosphate (cGMP)-specific phosphodiesterase type 5 (PDE5), such as sildenafil citrate) may also be helpful in the prevention of the severe vasoconstriction. However, a slower infusion rate may not be possible with respect to a trauma patient when demand for volume is acute and critical.

One mechanism of modifying the NO scavenging properties of hemoglobin based therapeutics is blocking of NO binding sites on these molecules. Unprotected thiol on the cysteine moiety of the hemoglobin may bind with NO. Protection of thiol or sulfhydryl groups in the hemoglobin molecule may prevent the binding of NO to the hemoglobin at the thiol site and hence prevent an acute vasoactive response of the blood vessels causing a hypertensive reaction. The prevention of NO binding to hemoglobin based therapeutics may also prevent interference with normal platelet aggregation and neutrophil migration when this class of therapeutics is administered.

Therefore, some of the desirable characteristics of hemoglobin based oxygen delivery therapeutics are: toxicity-free, lack of induction of harmful immunogenic response, satisfactory oxygen carrying and delivery capacity, suitable circulatory persistence to permit effective oxygenation of tissues, long shelf life, capacity for storage at room temperature, absence of viral or other pathogens to prevent disease transmission, elimination of the requirement for blood typing, and capacity for deployment by first responders such as, paramedics, front line military medics etc. These characteristics provide a rapid, safe response to blood loss and the immediate support of tissue metabolic needs, thus improving the chances for survival.

The present invention disclosed herein provides compositions, characteristics and methods to prepare deoxygenated, endotoxin free, stroma free, thiol blocked, cross-linked tetrameric hemoglobin which has low reactivity with Nitric Oxide (NO), and the tetrameric structures is stabilized by cross-linking. In particular a carboxamidomethylated cross linked tetrameric hemoglobin is provided as a stable NO blocked tetrameric Hb of the invention, as well as methods for its production. A process and methods of preparation of stable NO-blocked tetrameric Hb of the invention are disclosed as well as methods of use as blood volume expansion agents and as oxygen delivery therapy agents.

SUMMARY OF THE INVENTION

The present invention relates to a proteinaceous iron containing compound having a molecular weight distribution in the range of about 60,000 daltons to about 500,000 daltons and having at least one cysteine moiety wherein the cysteine moiety includes a thiol protecting group such that the proteinaceous compound has a reduced ability to bind nitric oxide at the cysteine site(s). In some embodiments, the proteinaceous iron containing compound transports oxygen with a p50 of about 20 mm Hg to about 45 mmHg. In some embodiments, the proteinaceous iron containing compound is incapable of binding nitric oxide at the cysteine site(s).

Another aspect of the invention relates to a composition comprising a proteinaceous iron containing compound having a molecular weight distribution in the range of about 60,000 daltons to about 500,000 daltons and having at least one cysteine moiety wherein the cysteine moiety includes a thiol protecting group such that the proteinaceous compound has a reduced ability to bind nitric oxide at the cysteine site(s).

Yet another aspect of the invention relates to a composition comprising a proteinaceous iron containing compound having a molecular weight distribution in the range of about 60,000 daltons to about 500,000 daltons and having at least one cysteine moiety wherein the cysteine moiety includes a thiol protecting group such that the proteinaceous compound has a reduced ability to bind nitric oxide at the cysteine site(s) and wherein said compound is a cross-linked tetrameric hemoglobin.

Another aspect of the invention relates to a process for a preparation of a tetrameric hemoglobin wherein the hemoglobin has a thiol protecting group attached to a cysteine group of the hemoglobin comprising: (a) removing endotoxin and other lipopolysaccharides from a preparation containing red blood cells; (b) lysing the red blood cells; (c) separating hemoglobin by removing stroma from the lysed red blood cells; (d) optionally removing oxygen from the hemoglobin; (e) adding to a hemoglobin solution a reagent which provides a thiol protecting group for a cysteine of the hemoglobin, and (f) separating a hemoglobin which has a thiol protecting group attached to a cysteine.

In some embodiments of the aforementioned aspect of the invention, the process further comprises: (a) optionally removing oxygen from the hemoglobin which has a thiol protecting group attached to a cysteine; and crosslinking the hemoglobin which has a thiol protecting group attached to a cysteine of the hemoglobin, yielding a stable NO-blocked tetrameric Hb of the invention, which is cross-linked.

In another aspect of the invention, a method for producing tetrameric hemoglobin is provided wherein a thiol protecting group is attached to a cysteine in the hemoglobin, by a process comprising: (a) removing endotoxin from a preparation containing red blood cells; (b) lysing said red blood cells; (c) separating hemoglobin by removing stroma from said lysed red blood cells; (d) optionally deoxygenating said hemoglobin; (e) adding to a hemoglobin solution a reagent which provides a thiol protecting group for a cysteine of said hemoglobin, and (f) separating a hemoglobin which has a thiol protecting group attached to a cysteine of the hemoglobin.

In another aspect of the invention, a method for producing a cross linked tetrameric hemoglobin is provided, by a process comprising: optionally removing oxygen from the product of the method for producting tetrameric hemoglobin; and crosslinking said product.

Yet another aspect of the invention relates to a method for producing a NO-blocked tetrameric hemoglobin wherein a thiol protecting group is attached to a cysteine in the hemoglobin, by a process comprising: (a) adding to the hemoglobin solution a reagent which provides a thiol protecting group for a cysteine of the hemoglobin, and (b) separating a hemoglobin which has a thiol protecting group attached to a cysteine of the hemoglobin. In some embodiments the hemoglobin is further cross-linked.

Another aspect of the invention relates to a method of supplementing the blood volume of a mammal comprising administering to the mammal a composition comprising a proteinaceous iron containing compound having a molecular weight of about 60,000 daltons to about 500,000 daltons and having at least one cysteine moiety wherein the cysteine moiety includes a thiol protecting group such that the proteinaceous compound has reduced ability to bind nitric oxide at the cysteine site(s), and further comprises a pharmaceutically acceptable carrier. In some embodiments the proteinaceous iron containing compound is cross-linked.

In another aspect of the invention, a method of treating a mammal suffering from a disorder is provided, comprising administering a composition comprising a proteinaceous iron containing compound having a molecular weight of about 60,000 daltons to about 500,000 daltons and having at least one cysteine moiety where the cysteine moiety includes a thiol protecting group such that the proteinaceous compound has reduced ability to bind nitric oxide at the cysteine site(s). In some embodiments the proteinaceous iron containing compound is cross-linked.

In another aspect of the invention, a method is provided for perfusing an organ comprising administering an effective amount of the stable NO-blocked tetrameric hemoglobins of the invention, which can further be performed in-vivo or ex-vivo.

In some embodiments, the proteinaceous iron containing compound increases oxygen offloading capacity relative to native, cell free hemoglobins. In some embodiments, the proteinaceous iron containing compound increases oxygen delivery ability. In some embodiments, the crosslinked tetrameric hemoglobin is materially reduced in its ability to bind nitric oxide. In some embodiments the cross linked tetrameric hemoglobin is incapable of binding nitric oxice. In some preferred embodiments, the crosslinked tetrameric hemoglobin transports oxygen with a p50 of about 20 mm Hg to about 45 mm of Hg. In some embodiments the proteinaceous iron containing compound transports oxygen with a p50 of about 20 mm Hg to about 45 mm of Hg.

In some embodiments of the invention, the proteinaceous iron containing compound is a thiol-protected hemoglobin. In some embodiments, the proteinaceous iron containing compound is a cross-linked tetrameric hemoglobin. In some embodiments, the proteinaceous iron containing compound has been crosslinked with bis 3',5' dibromo salicyl fumarate. In some embodiments, the hemoglobin has been modified by reaction with pyridoxal-5'-phosphate. In some embodiments, the hemoglobin is mammalian. In some embodiments, the hemoglobin is human hemoglobin. In some embodiments, the hemoglobin is bovine (i.e. bovine (genus *bos*) or bison (genus *bison*)) or porcine hemoglobin. In some preferred embodiments, the hemoglobin is non-pyrogenic, endotoxin free, oxygen free and stroma free, enzyme free, and with low induction of negative immunogenic reactions.

In some preferred embodiments, oxygen is removed from hemoglobin which may or may not have a thiol protecting group attached to a cysteine of the hemoglobin. In some embodiments the oxygen is removed by contactor membrane technology.

In another aspect of the invention, the proteinaceous iron containing compound of the invention is a thiol blocked stroma free hemoglobin that may be safely stored for extended periods. This thiol blocked stroma free hemoglobin may be a stable intermediate which can endure packaging, shipping and further handling to yield another hemoglobin composition of the invention. In some embodiments the stable intermediate is further optionally deoxygenated, crosslinked, and purified to remove excess reagents and byproducts of the reaction, for example, dibromo salicylic acid. In some embodiments the stable NO blocked tetrameric hemoglobin is packaged.

In other embodiments of the invention, the compound is non-pyrogenic, endotoxin free, and stroma free. In some embodiments of the invention is proteinaceous compound is of low viscosity. In some embodiments the proteinaceous compound of the invention is oxygen free.

In some embodiments, the reagent that provides a thiol protecting group is selected from the group consisting of 4-pyridylmethyl chloride, alkoxyalkylchloride, dimethoxymethane, N-(hydroxymethyl)acetamide, triphenylmethyl chloride, acetyl chloride, acetic anhydride, haloacetamide, iodoacetate, benzyl chloride, benzoyl chloride, di-tert-butyl dicarbonate, p-hydroxyphenacyl bromide, p-acetoxybenzyl chloride, p-methoxybenzyl chloride, 2,4-dinitrophenyl fluoride, tetrahydropyran, acetamidohydroxymethane, acetone, bis-carboethoxyethene, 2,2,2-trichloroethoxycarbonyl chloride, tert-butoxycarbonyl chloride, alkyl isocyanate, and alkoxyalkyl isocyanate. In some preferred embodiments, the haloacetamide is iodoacetamide. In some embodiments, the thiol protecting group is selected from the group consisting of 4-pyridylmethyl, acetylaminomethyl, alkoxyalkyl, triphenylmethyl, derivatives of carboxymethyl, carboxamidomethyl, acetyl, benzyl, benzoyl, tert-butoxycarbonyl, p-hydroxyphenacyl, p-acetoxybenzyl, p-methoxybenzyl, 2,4-dinitrophenyl, isobutoxymethyl, tetrahydropyranyl, acetamidomethyl, benzamidomethyl, bis-carboethoxyethyl, 2,2,2-trichloroethoxycarbonyl, tert-butoxycarbonyl, N-alkyl carbamate, and N-alkoxyalkyl carbamate. In some embodiments, the thiol protecting group is a carboxamidomethyl group.

Some embodiments of the invention provide compositions comprising the proteinaceous iron containing compound and a pharmaceutically acceptable carrier. In some embodiments provide a container containing a composition comprising the proteinaceous compound of the invention, optionally comprising a pharmaceutically acceptable carrier.

In some embodiments, the mammal suffers from acute anemia, anemia related conditions, hypoxia or ischemia. In some embodiments, the mammal needs volume transfusion of a blood substitute for transport of oxygen. In some embodiments, the mammal is in trauma and has suffered an acute volume loss.

In some embodiments of the methods of the invention, administration is made by implant, injection or transfusion.

In other embodiments of the method of the invention, the mammals are suffering from a disorder including anemia, anemia related conditions, hypoxia and ischemia. The anemia and anemia related conditions may be caused by renal failure, diabetes, AIDS, chemotherapy, radiation therapy, hepatitis, G.I. blood loss, iron deficiency, or menorrhagia. In some embodiments of the invention, the method includes administering erythropoietin therapy In some embodiments of the method of the invention, the disorder being treated is ischemia, which is caused by burns, stroke, emerging stroke, transient ischemic attacks, myocardial stunning and hibernation, acute angina, unstable angina, emerging angina, or infarct. In other embodiments of the method, the disorder is carbon monoxide poisoning.

In other embodiments of the method of the invention, the disorder that the mammal is treated for is recovery after surgery. In some other embodiments of the method of the invention, the disorder is diabetic wound healing. In yet other embodiments of the method the disorder is sickle cell anemia, and the administration may further be made prior to surgery. In other embodiments of the method of the invention, the disorder is acute coronary syndrome. In other embodiments of the method of the invention, the disorder is cardiogenic shock.

In some embodiments of the method of the invention the proteinaceous iron containing compound is administered to a mammal in need of a blood transfusion. In some embodiments of the invention, the mammal is suffering from trauma. In some embodiments of the method, the disorder that the mammal is suffering from is lack of oxygen delivery capacity is caused by environmental stress or physical stress.

In other embodiments of the method of the invention, the proteinaceous iron containing compound is administered in combination with radiation therapy. In yet other embodiments of the invention, the method further comprises administering to said mammal an oxygen dependent pharmaceutical agent.

In some embodiments of the method of the invention, administering the proteinaceous iron containing compound to said mammal permits visualization of intravascular space in-vivo, while maintaining oxygenation of the tissue within the viewing field.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

The patent or application file contains at least one drawing executed in color. Copies of this patent or patent application publication with color drawing(s) will be provided by the Office upon request and payment of the necessary fee.

FIG. 4B depicts overlays of the electrophoretic separation of native hemoglobin, dXCMSFH, and size standards for the full electropherogram.

FIG. 5 depicts the HLPC size exclusion separation of products of the cross linking reaction.

FIG. 6 shows oxygen affinity curves for bovine whole blood, stroma free Hb, cross linked hemoglobin, and fresh human blood.

DETAILED DESCRIPTION OF THE INVENTION

Figure 1:
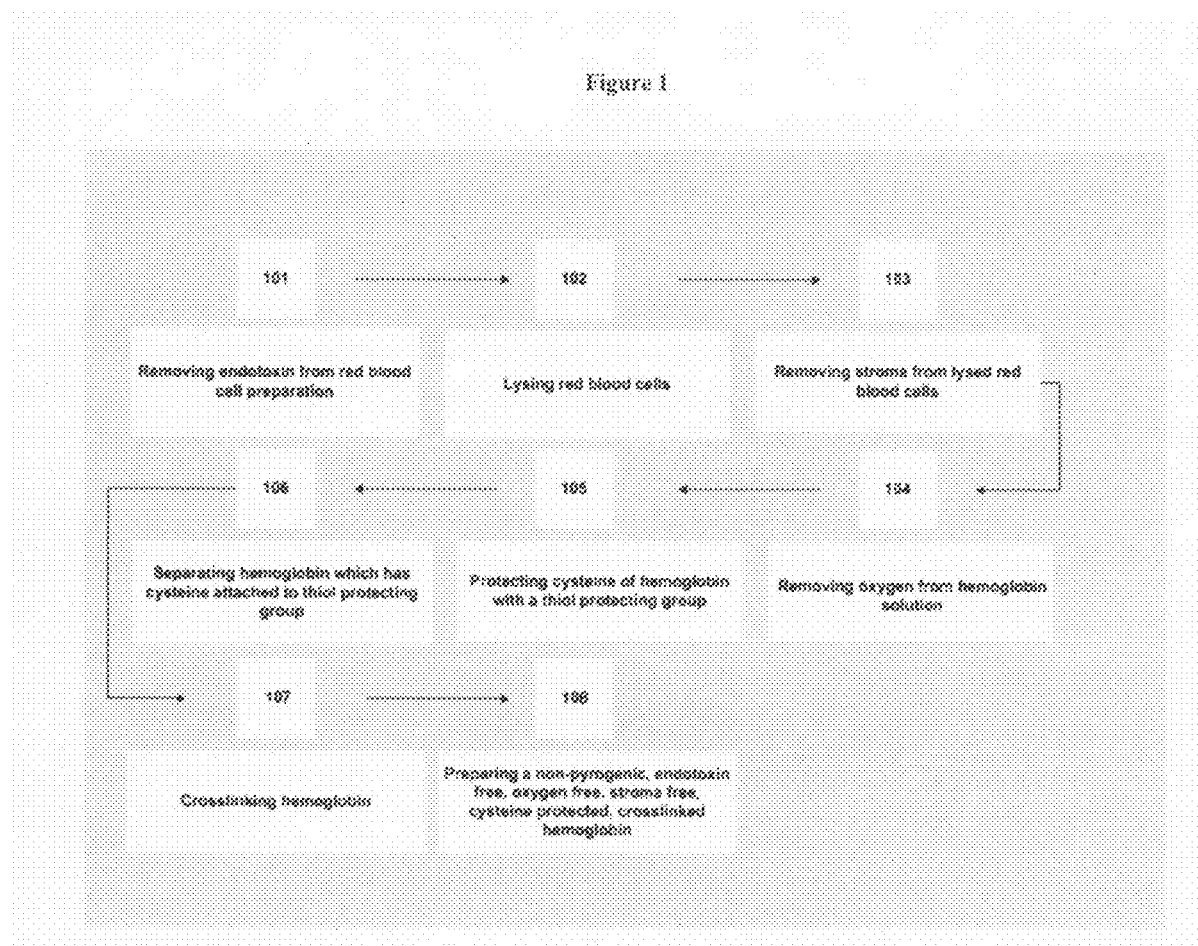
FIG. 1 is a flow chart showing the steps of the methods as disclosed herein.

The term "endotoxin free" or its grammatical equivalents as used herein, means a hemoglobin that has been treated to reduce exposure to and to remove substantially or completely all endotoxin as measured by a very sensitive assay technique such as a tubidometric assay or a chromogenic assay. These methods are capable of detecting less than 0.05 EU per ml. Thus, endotoxin-free hemoglobin can have less than or the equivalent of the amount of endotoxin present in Water for Injection (WFI).

The term "non-pyrogenic" or its grammatical equivalents as used herein, means a hemoglobin that may be administered to a mammal without causing IL-8 overproduction, complement activation, platelet activation, inflammatory response or a febrile reaction.

The term "oxygen free", "deoxygenated", or its grammatical equivalents as used herein, means a hemoglobin that has been treated to remove substantially or completely all oxygen bound to the heme pocket. Oxygen-free hemoglobin thus is substantially or completely in the higher energy "tense" or "T" configuration.

The term "stroma free" or its grammatical equivalents as used herein, means a hemoglobin that has been treated or processed to remove substantially or completely all stromal material, such that the preparation no longer exhibits the immunoreactivity to red cell surface type antigens characteristic of RBC membranes. Stroma are the cell membrane structural proteins and removing stroma also will remove antigens associated with the cell membrane. Stroma-free hemoglobin therefore substantially or completely lacks the toxic and/or pyrogenic properties associated with preparations of hemolyzed red blood cells still containing portions of the lipid membrane surrounding the hemoglobin protein, and thus after molecular stabilization, this stabilized stroma free hemoglobin can be administered to an individual without causing transfusion reaction toxicity or inflammatory reaction.

The term "NO-blocked tetrameric Hb" refers to endotoxin-free, stroma-free thiol blocked tetrameric hemoglobins of the present invention. The term "stable NO-blocked tetrameric Hb" refers to the cross-linked, endotoxin-free, stroma free, thiol blocked hemoglobins of the present invention.

The term "dNO-blocked tetrameric Hb" refers to the deoxygenated endotoxin-free, stroma-free, thiol blocked, cross-linked hemoglobins of the present invention. One embodiment of this class of compounds is "dXCMSFH", which is a specific example of a deoxygenated endotoxin-free, stroma-free, carboxamidomethylated cross linked hemoglobin of the present invention.

The term "dTBSFH" refers to the deoxygenated endotoxin-free, stroma-free, thiol-blocked uncross-linked hemoglobin of the present invention.

The term "dCMSFH refers to the deoxygenated endotoxin-free, stroma free, carboxamidomethylated uncross-linked hemoglobin of the invention and is a specific example of a dTBSFH.

The term "mammal" refers to both human and non-human animals.

The compositions and methods of the present invention relate to a thiol-protected, cross-linked tetrameric hemoglobin (stable NO blocked Hb) where at least one cysteine moiety in the hemoglobin molecule includes a thiol protecting group, for example, a carboxamidomethyl group, such that the thiol group in the cysteine moiety is not available for binding with nitric oxide (NO). Preferably, at least two cysteine moieties in the hemoglobin are protected with a thiol (or sulfhydryl) protecting group such that the thiol group in the cysteine moiety is not available for binding with nitric oxide (NO). These NO-blocked hemoglobins disclosed herein prevent vasoactive reactions of blood vessels when administered. The stable NO-blocked tetrameric hemoglobins of the invention are further cross linked to provide an oxygen carrying capacity with a p50 of about 20 mm Hg to about 45 mm Hg and an extended circulatory half life. Preferably, the hemoglobin is non-pyrogenic, endotoxin free, oxygen free, and stroma free. Therefore, thiol-protected cross-linked hemoglobins of the present invention (a stable NO-blocked tetrameric Hb) have high oxygen exchange capacity and are functionally superior to native hemoglobin.

I. Hemoglobin Compositions

1. Hemoglobin Sources and Molecular Structure

Hemoglobin (or blood or RBCs which it may be isolated from) used in the present invention may be obtained from a variety of mammalian sources, such as, for example, human, bovine (genus *bos*), bison (genus *bison*), ovine (genus *ovis*), porcine (genus *sus*) sources, other vertebrates or transgenically-produced hemoglobin. Alternatively, the stroma-free hemoglobin used in the present invention may be synthetically produced by a bacterial, or more preferably, by a yeast, mammalian cell, or insect cell expression vector system (Hoffman, S. J. et al., U.S. Pat. No. 5,028,588 and Hoffman, et al., WO 90/13645, both herein incorporated by reference). Alternatively, hemoglobin can be obtained from transgenic animals; such animals can be engineered to express non-endogenous hemoglobin (Logan, J. S. et al. PCT Application No. PCT/US92/05000; Townes, T. M. et al., PCT Application No. PCT/US/09624, both herein incorporated by reference in their entirety). Preferably, the stroma-free hemoglobin used in the present invention is isolated from bison, bovine or human sources.

The genus *bos* includes, subgenus *bos* including *bos taurus* (western cattle, including oxen and aurochs) and *bos aegyptiacus;* subgenus *bibos* including *bos frontalis* (gaur, gayal or Indian bison) and *bos javanicus* (banteng); subgenus *novibos* including *bos sauveli* (kouprey or grey ox), and; subgenus *poephagus* including *bos grunniens* (yak; also *bos mutus*). The *bos taurus*, includes similar types from Africa and Asia such as, *bos indicus,* the zebu; and the *bos primigenius,* the aurochs. The *bos gurus* includes subspecies, *bos gaurus laosiensis, bos gaurus gaurus* (such as in India, Nepal) also called "Indian bison", *bos gaurus readei, bos gaurus hubbacki* (such as in Thailand, Malaysia), and *bos gaurus frontalis,* a domestic gaur, or a gaur-cattle hybrid breed.

*Bison* is a taxonomic genus containing six species within the subfamily bovinae. The bison may be called buffalo in Asia (such as water buffalo) and Africa (such as African buffalo). The genus bison includes species such as, *bison latifrons* (long-horned bison), *bison antiquus, bison occidentalis, bison priscus, bison bison, bison bison bison, bison bison athabascae, bison bonasus, bison bonasus bonasus, bison bonasus caucasicus,* and *bison bonasus hungarorum*. In some embodiments of the present invention, the hemoglobin is from genus *bos* or *bison* It shall be understood that any mammalian species may be used as a source of hemoglobin and is within the scope of the present invention.

Bovine Hb is easier to obtain and more abundant than human Hb. Typically human Hb extracted from outdated RBCs is used for Hb-based artificial blood research. However, outdated RBCs are not available in sufficient quantities to produce large amounts of viable oxygen delivery therapeutics or blood substitutes.

Hemoglobin, whether derived from an animal, synthetic or recombinant, may be composed of the "naturally existing" hemoglobin protein, or may contain some or be entirely composed of, a mutant hemoglobin protein. Preferred mutant hemoglobin proteins include those whose mutations result in more desirable oxygen binding/release characteristics. Examples of such mutant hemoglobin proteins include those provided by Hoffman, S. L. et al. (U.S. Pat. Nos. 5,028,588 and 5,776,890) and Anderson, D. C. et al . (U.S. Pat. Nos. 5,844,090 and 5,599,907), all herein incorporated by reference in their entirety.

Hemoglobin or haemoglobin (Hb) is a proteinaceous heme iron-containing compound having a molecular weight of about 60,000 daltons which transports oxygen in the red blood cells of the blood in mammals and other animals. Hemoglobin transports oxygen from the lungs to the rest of the body, such as to the muscles, wherein it releases part of the oxygen load. The hemoglobin molecule is an assembly of four globular protein subunits. Each subunit is composed of a protein chain tightly associated with a non-protein heme group. Each individual protein chain arranges in a set of α-helix structural segments connected together in a "myoglobin fold" arrangement, so called because this arrangement is the same folding motif used in the heme/globin proteins. This folding pattern contains a pocket which is suitable to strongly bind the heme group. A heme group consists of an iron atom held in a heterocyclic ring, known as a porphyrin. These iron atoms are the sites of oxygen binding. The iron atom is bonded equally to all four nitrogens in the center of the ring, which lie in one plane. Two additional bonds perpendicular to the plane on each side can be formed with the iron to form the fifth and sixth positions, one connected strongly to the protein, the other available for binding of oxygen. The iron atom can either be in the $Fe^{2+}$ or $Fe^{3+}$ state, but ferrihaemoglobin (methemoglobin) ($Fe^{3+}$) cannot bind oxygen.

In adult humans, the predominate hemoglobin type is a tetramer (which contains 4 subunit proteins) called hemoglobin A, consisting of two α and two β subunits non-covalently bound, each made of 141 and 146 amino acid residues, respectively. This is denoted as $\alpha_2\beta_2$. The subunits are structurally similar and about the same size. Each subunit has a molecular weight of about 16,000 daltons, for a total molecular weight of the tetramer of about 64,000 daltons. The four polypeptide chains are bound to each other by salt bridges, hydrogen bonds and hydrophobic interactions. There are two kinds of contacts between the α and the β chains: $\alpha_1\beta_1$ and $\alpha_1\beta_2$. However, adult hemoglobin may also comprise δ globin subunits. The δ globin subunit replaces β globin and pairs with α globin as $\alpha_2\delta_2$ to form hemoglobin A2.

Bovine Hb is structurally similar to human Hb. The bovine Hb also contains two α chains and two β chains, with similar molecular weight distribution.

2. Protecting the Sulfhydryl Groups of the Cysteine of the Hemoglobin

A thiol group of a cysteine moiety in a hemoglobin may bind to nitric oxide and may result in transient or sustained changes in hemodynamic properties of blood or vasoactive substances and may lead to hypertensive reactions. This occurrence can be avoided by protecting the thiol group of the cysteine moiety in the hemoglobin such that the resulting hemoglobin is incapable of binding with NO.

Bovine hemoglobin contains only two thiol groups (Cys 93 on each of the beta chains) which are involved in binding NO. Hence preferably, both thiol groups are protected with a thiol protecting group in bovine Hb. Human hemoglobin contains six thiol groups ($\alpha$ Cys 104, $\beta$Cys 93, and $\beta$ Cys 112), and at least two of which (Cys 93 on each of the beta chains) are involved in binding NO. Preferably these two thiols are protected and up to six thiol groups may be protected with a thiol protecting group in human Hb.

The SFH of the present invention can be reacted with various reagents to result in protection of the thiol group in the cysteine moiety of the hemoglobin. Without limiting the scope of the present invention, all the reagents known in the art for the protection of a functional group such as, but not limited to, hydroxyl, thiol, or carboxyl, are included in the present invention.

Some of the examples of the reagents include, but are not limited to, 4-pyridylmethyl chloride, alkoxyalkylchloride, dimethoxymethane, N-(hydroxymethyl)acetamide, triphenylmethyl chloride, acetyl chloride, 2-chloroacetic acid, acetic anhydride, haloacetamide such as, iodoacetamide, bromoacetamide, chloroacetamide, or fluoroacetamide, haloacetate such as iodoacetate, bromoacetate, chloroacetate, or fluoroacetate, benzyl chloride, benzoyl chloride, di-tert-butyl dicarbonate, p-hydroxyphenacyl bromide, p-acetoxybenzyl chloride, p-methoxybenzyl chloride, 2,4-dinitrophenyl fluoride, tetrahydropyran, acetamidohydroxymethane, acetone, bis-carboethoxyethene, 2,2,2-trichloroethoxycarbonyl chloride, tert-butoxycarbonyl chloride, alkyl isocyanate, and alkoxyalkyl isocyanate. In a preferred embodiment, the reagent is haloacetamide. In a further preferred embodiment, the reagent is iodoacetamide. It is understood that any reagent known in the art that can be used for carboxamidomethylation of the thiol group in the cysteine moiety of the hemoglobin is within the scope of the present invention.

Without limiting the scope of the present invention, all the protecting groups known in the art for the protection of a functional group such as, but not limited to, hydroxyl, thiol, or carboxyl, are included in the present invention. Some of the examples of the protecting group include, but are not limited to, 4-pyridylmethyl, acetylaminomethyl, alkoxyalkyl, triphenylmethyl, carboxamidomethyl, acetyl, benzyl, benzoyl, tert-butoxycarbonyl, p-hydroxyphenacyl, p-acetoxybenzyl, p-methoxybenzyl, 2,4-dinitrophenyl, isobutoxymethyl, tetrahydropyranyl, acetamidomethyl, benzamidomethyl, bis-carboethoxyethyl, 2,2,2-trichloroethoxycarbonyl, tert-butoxycarbonyl, N-alkyl carbamate, and N-alkoxyalkyl carbamate. In a preferred embodiment, the protecting group is carboxamidomethyl such that the protection of the thiol group in the cysteine moiety of the hemoglobin results in a non-pyrogenic, endotoxin free, stroma free, carboxamidomethylated Hb (CMSFH or a stable NO blocked Hb). More generally, protection of the thiol group in cysteine(s) of hemoglobin results in a non-pyrogenic, endotoxin free, stroma free thiol blocked Hb (TBSFH or an NO blocked Hb).

3. Oxygen Affinity Modulation and Stabilization by Cross Linking within Tetrameric Hemoglobin.

Bovine Hb and human Hb differ in the way in which oxygen affinity is modulated. In the tetrameric form of normal adult human hemoglobin, the binding of oxygen is a cooperative process. The binding affinity of hemoglobin for oxygen is increased by the oxygen saturation of the molecule. As a consequence, the oxygen binding curve of hemoglobin is sigmoidal, or S-shaped. This positive cooperative binding may be achieved through steric conformational changes of the hemoglobin protein complex. When one subunit protein in hemoglobin becomes oxygenated, it induces a conformational or structural change in the whole complex causing the other subunits to gain an increased affinity for oxygen.

When hemoglobin binds oxygen, it shifts from the high energy "tense" or "T" state (deoxygenated or oxygen free) to the lower energy "relaxed" or "R" state (oxygenated). Human $\alpha$ and $\beta$ globin genes have been cloned and sequenced (Liebhaber et al., *Proc. Natl. Acad. Sci.* (U.S.A). 77:7054-58 (1980); Marotta et al., *J. Biol. Chem.* 252:5040-43 (1977); and Lawn et al., *Cell* 21:647 (1980), all of which are incorporated by reference in their entirety). The tetrameric structure of human T state deoxyhemoglobin has increased stability from six ionic bonds and while in the T state, hemoglobin is effectively prevented from disassociating into dimers. In this conformation, the beta cleft contact area between the two beta chains (also known as the beta pocket, phosphate pocket, and 2,3-diphosphoglycerate binding site) in deoxyhemoglobin is substantially different than in oxyhemoglobin. The changed conformation of the beta cleft in the T state is believed to explain the decreased oxygen affinity stabilized by 2,3-diphosphoglycerate. The T state of hemoglobin is stable and resistant to denaturation.

Inside red blood cells, the binding of 2,3-diphosphoglycerate to its binding site within human hemoglobin decreases the hemoglobin's oxygen affinity to a level compatible with oxygen transport and delivery in a physiologic range of pH 7.2 to 7.4. The binding of 2,3-diphosphoglycerate to hemoglobin is weak and may require high concentrations (i.e., concentrations approaching 1M or more) in order to modify the oxygen affinity of hemoglobin. For example, in people acutely acclimated to high altitudes, the concentration of 2,3-diphosphoglycerate (2,3-DPG) in the blood is increased, which allows these individuals to release a larger amount of oxygen to tissues under conditions of lower oxygen tension.

Thus, when the red blood cells are ruptured to produce stroma free hemoglobin (SFH), the 2,3-diphosphoglycerate may not be retained in close proximity to the hemoglobin and may disassociate from the hemoglobin. As a consequence, unless further modified, Human SFH may exhibit a higher affinity for oxygen than does hemoglobin in RBCs. The p50 of stroma free human hemoglobin in solution can be approximately 12 to 17 mm Hg as compared to native, RBC associated hemoglobin p50 of approximately 27 mm Hg. The increased affinity of the SFH for oxygen, under physiological conditions, may prevent high capacity release of the bound oxygen to the tissues.

In contrast, bovine Hb, possessing a further internal salt bridge, has its affinity for oxygen affected by the ionic strength of the local environment. Bovine hemoglobin does not require 2,3-DPG to maintain a p50 for oxygen in the range of 30 mm Hg to 40 mm Hg. An advantage to affinity modulation by altering ionic strength versus that induced by 2,3-DPG binding is that sufficient concentration of ionic species is generally present in plasma while 2,3-DPG is only contained within RBCs. Thus, the oxygen affinity of acellular bovine Hb can be modulated more easily than acellular human Hb.

This advantage of modulation of affinity by general ionic interaction can be built back into human Hb by reacting it with pyridoxal-5-phosphate (PLP). PLP modifies human Hb by introducing a negative charge near a penultimate β chain histidine residue and by removing a positive charge at the amino terminal end of the same chain, An altered human Hb of this class can now respond more similarly to bovine Hb to charged species in the local environment and not solely depend on binding of 2,3-DPG to affect oxygen affinity.

Within the RBC, the association of the α chain with its corresponding β chain is very strong and does not disassociate under physiological conditions. The association of one α/β dimer with another α/β dimer, however, is fairly weak and outside of the RBC, the two dimers may disassociate even under physiological conditions. Upon disassociation, the dimer is filtered through the glomerulus. The rapid clearing of stroma free hemoglobin (SFH) by the kidney is a consequence of its quaternary molecular arrangement.

To avoid such removal of human and bovine hemoglobin alike, cell-free hemoglobin can be conjugated or cross-linked by various methods known in the art. One of the methods is by conjugating Hb to another molecule such as polyethylene glycol (PEG), which forms a hydrophilic shield around the Hb molecule and simultaneously increases its size which in turn increases its circulatory half-life. Hb can also be cross-linked intramolecularly to prevent dissociation of the tetramer into αβ dimers and/or cross-linked intermolecularly to form polymers which also increases the oxygen carrier's size and thus increases its circulatory half-life. Using site-specific cross-linking reagents, intramolecular covalent bonds may be formed, which may convert Hb into a stable tetramer, thus preventing its dissociation into αβ dimers. On the other hand, the use of non-specific cross-linkers such as glutaraldehyde may lead to non-specific covalent bonding between amino acid residues residing within and between Hb tetramers. This leads to the formation of hemoglobin polymers (polyHb) of various molecular weights and oxygen affinities. Chemical reagents with multi-aldehyde functionalities can be used as cross-linking agents. These include molecules such as glutaraldehyde, ring-opened raffinose and dextran. In the case of aldehydes, the formation of covalent cross-links may be initiated by the carbonyl group of the aldehyde reacting with an amino group present in the Hb tetramer. Polymerization of Hb into larger molecules may increase the intravascular half-life of the polyHb with respect to native tetrameric Hb and prevent Hb dissociation into αβ dimers. PolyHb may be eventually filtered out of the systemic circulation throughout the kidneys, the lymphatic system, and the reticuloendothelial system (RES).

Several other chemical agents can be used to cross-link hemoglobin α/β dimers and prevent their filtration by the glomerulus into the urine, and yet maintain the oxygen transport and delivery properties of native hemoglobin. Bis 3',5'dibromo salicyl fumarate (DBSF) is an activated diester of fumaric acid that has been used as a cross-linker to cross-link hemoglobin (Tye, U.S. Pat. No. 4,529,719, hereby incorporated by reference in its entirety). Bis 3',5'dibromo salicyl fumarate effects this change by associating the salicyl moieties with the sites known to bind aspirin within hemoglobin, and then effecting cross linking by the fumarate active functionalities with the alpha and beta chains. This maintains the two dimers in proper orientation for cross-linking with lysine residues. Cross-linking the α or β chains to a like chain of the other half of the tetramer forming hemoglobin can prevent disassociation of the tetramer and yields stable hemoglobins of the invention with a oxygen carrying capacity with a p50 of about 20 mm Hg to about 45 mm Hg, with a p50 test performed in vitro in the absence of $CO_2$. Cross linking is also possible between unlike chains in opposing dimeric pairs. Thus cross linking hemoglobin can address both the issues of oxygen affinity, by locking the conformation of the modified hemoglobin into the T state, and the problem of rapid filtration by the kidney.

Hemoglobin's oxygen-binding capacity may be decreased in the presence of carbon monoxide because both gases compete for the same binding sites on hemoglobin, carbon monoxide binding preferentially relative to oxygen. Hemoglobin binding affinity for CO is 200 times greater than its affinity for oxygen, meaning that small amounts of CO may reduce hemoglobin's ability to transport oxygen. When hemoglobin combines with CO, it forms a very bright red compound called carboxyhemoglobin. When inspired air (i.e., for example in the environment of tobacco smoking, cars, and furnaces) contains CO levels as low as 0.02%, headache and nausea may occur; if the CO concentration is increased to 0.1%, unconsciousness may follow. In heavy smokers, up to 20% of the oxygen-active sites can be blocked by CO. Hemoglobin also has competitive binding affinity for sulfur monoxide (SO), nitrogen dioxide ($NO_2$), nitric oxide (NO), and hydrogen sulfide ($H_2S$). The iron atom in the heme group is in the $Fe^{2+}$ oxidation state to support oxygen transport. Oxidation to $Fe^{3+}$ state converts hemoglobin into methemoglobin, which cannot bind oxygen. Nitrogen dioxide and nitrous oxide are capable of converting hemoglobin to methemoglobin.

Carbon dioxide occupies a different binding site on the hemoglobin. Hemoglobin can bind protons and carbon dioxide, causing a conformational change in the protein and facilitating the release of oxygen. Protons bind at various sites along the protein and carbon dioxide binds at the α-amino group, hence forming carbamate. Conversely, when the carbon dioxide levels in the blood decrease (i.e., around the lungs), carbon dioxide is released, increasing the oxygen affinity of the protein. This control of hemoglobin's affinity for oxygen by the binding and release of carbon dioxide is known as the Bohr effect.

As described above, the conformational change affected by the change in proton binding to hemoglobin facilitates oxygen offloading in tissues where the carbon dioxide concentration is increasing, with resultant pH decrease. This creates a leftward shift of the cooperativity curve for hemoglobin's affinity for oxygen, yielding greater efficiency in delivery of oxygen per gram of hemoglobin. Enhancing this shift in a modified hemoglobin may result in an effective therapeutic intervention for patients with poor cardiac function, thus providing more effective oxygenation with less work required by the heart. Additionally, a hemoglobin so modified to yield superior oxygen offloading can be useful in treating patients subject to performance related oxygenation deficits.

II. Methods For Producing Carboxamidomethylated Cross-Linked Hemoglobin

The steps for some of the embodiments of the present invention are depicted in FIG. 1. Without limiting the scope of the present invention, the steps can be performed independently of each other or one after the other. One or more steps can be deleted in the methods of the present invention. The method of producing the hemoglobin of the present invention can include step 101 comprising removing plasma proteins and endotoxin from a preparation containing red blood cells by washing; step 102 comprising lysing the red blood cells; step 103 comprising separating hemoglobin by removing stroma, including membranes and leucocytes, from the lysed red blood cells; step 104 comprising removing oxygen from the hemoglobin; step 105 comprising adding to a hemoglobin solution a reagent which provides a thiol protecting group for a cysteine of the hemoglobin; step 106 comprising separating the hemoglobin which has a thiol protecting group attached to a cysteine group of the hemoglobin; step 107 comprising cross linking the hemoglobin; and step 108 comprising equilibrating the hemoglobin in biologically compatible buffer and preparing a non-pyrogenic, endotoxin free, oxygen free, stroma free, cysteine protected, cross linked hemoglobin. Without limiting the scope of the present invention, the order of the steps may be changed depending on the requirements for producing a hemoglobin according to this invention.

1. Materials and Equipment Preparation

Whole blood from bovine sources may be obtained from live or freshly slaughtered donors. Upon collection, the blood is typically mixed with at least one anticoagulant to prevent significant clotting of the blood. Suitable anticoagulants for blood are as classically known in the art and include, for example, sodium citrate, ethylenediaminetetraacetic acid and heparin. When mixed with blood, the anticoagulant may be in a solid form, such as a powder, or in an aqueous solution. It is understood that the blood solution source can be from a freshly collected sample or from an old sample. The methods of the invention provide for the use of expired human blood from a blood bank. Further, the blood solution could previously have been maintained in frozen and/or liquid state. It is preferred that the blood solution is not frozen prior to use in this method.

Prior to introducing the blood solution to anticoagulants, antibiotic levels in the blood solution, such as penicillin, may be assayed. Antibiotic levels may be determined to provide a degree of assurance that the blood sample is not burdened with an infecting organism by verifying that the donor of the blood sample was not being treated with an antibiotic. Alternatively, a herd management program to monitor and insure the lack of disease in or antibiotic presence from treatment of the cattle may be used. The blood solution may be strained prior to or during the anticoagulation step, for example by straining, to remove large aggregates and particles. A 150 micron filter is a suitable strainer for this operation.

Any of a variety of assays may be employed to demonstrate the non-pyrogenicity of the compositions of the present invention, for example, but are not limited to, interleukin-6 and other cytokine induction (Pool, E. J. et al., *J. Immunoassay* 19:95-111 (1998), and; Poole, S. et al., *Dev. Biol. Stand.* 69:121-123 (1988)); human monocytoid cell line assays (Eperon, S. et al., *J. Immunol. Meth.* 207:135-145 (1997), and; Taktak, Y. S. et al., *J Pharm. Pharmacol.* 43:578-582 (1991)); the limulus amoebocyte lysate (LAL) test (Fujiwara, H. et al., *Yakugaku Zasshi* 110:332-40 (1990), and; Martel F. et al., *Rev Fr Transfus Immunohematol* 28:237-250 (1985)) and the rabbit pyrogen test (Bleeker W. K. et al., *Prog Clin Biol Res* 189:293-303 (1985); Simon, S. et al., *Dev. Biol. Stand.* 34:75-84 (1977), and; Allison, E. S. et al., *Clin. Sci. Mol. Med.* 45:449-458 (1973)), all references incorporated herein in their entirety. The rabbit pyrogen test was the preferred pyrogenicity assay until enhanced LAL-testing has replaced this former technique. It is understood that other methods of removing pyrogen are known in the art and are within the scope of the present invention, including filters, absorbers, affinity materials, etc.

Serum lipases, such as lipase A, do not inactivate endotoxins bound to the hemoglobin molecule. Therefore, endotoxins remain active toxins when taken up by the hepatocyte metabolizing the hemoglobin. Friedman, H. I. et al. reported triad hepatoxicity in a rat model consistent with this theory (See, Friedman, H. I. et al., *Lab Invest* 39:167-77 (1978), and; Colpan et al., U.S. Pat. No. 5,747,663) have reported a process for reducing or removing endotoxins from a cellular lysate solution. Wainwright et al. (U.S. Pat. No. 5,627,266) have described an endotoxin binding protein immobilized to a solid support and the use of this molecule in the removal of endotoxins from solution.

In some embodiments of the present invention, the elimination of contamination with endotoxins can be ensured by preventing the introduction of endotoxins to the chemical processes of the present invention. Typically, endotoxins are added inadvertently by using endotoxin contaminated water, non-sterile techniques, or the simple process of bacteria exposure during collection. Measurement of endotoxins can be difficult, and standard LAL binding assays do not work in the presence of hemoglobin since initial collection endotoxin binds strongly to hemoglobin. However, turbidometric, and chromogenic assays have been validated that allow for very low limits of detection. Water and the blood collection can be the most likely candidates for introduction of endotoxins since increased number of steps in the preparation of hemoglobin may increase the level of toxicity. Preparations using dialysis and filtration methods can expose the hemoglobin to a thousand volumes of water/buffer that may be contaminated with endotoxin. Membrane systems may be pretreated with NaOH or NaOCl to reduce or eliminate endotoxins. These materials may then be flushed and cleaned from the various devices.

It is preferred that all membranes, and equipment used to produce the hemoglobin of the present invention be cleansed in a manner sufficient to cause the removal or elimination of endotoxin that may be present on such materials and equipment. Preferably, such cleansing is accomplished by pre-washing surfaces and equipment that may come into contact with the hemoglobin of the present invention using a dilute solution of hemoglobin, previously qualified as non-endotoxin bearing. Such a solution serves to bind endotoxin and hence to remove residual endotoxin that may be present on such membranes or equipment. See, for example, Tye, U.S. Pat. No. 6,894,150. The dilute solution of hemoglobin used for washing is discarded after each use. Preferably, any ion removal or buffer equilibration can be performed using counter flow dialysis so as to prevent accumulation of endotoxin in the subsequent product.

2. Step 101. Washing of RBCs to remove Plasma Proteins and endotoxin. The RBCs in the blood solution can be washed by any suitable means, such as by diafiltration or by a combination of discrete dilution and concentration steps with at least one solution, such as an isotonic solution, to separate RBCs from extracellular plasma proteins, such as serum albumins or antibodies (e.g., immunoglobulins (IgG)). It is understood that the RBCs can be washed in a batch or continuous feed mode. Acceptable isotonic solutions are well known in the art and include solutions, such as, for example, citrate/saline solution or PBS which have a pH and osmolarity which does not rupture the cell membranes of RBCs and displaces the plasma portion of the whole blood. Sources of purified water which can be used in the method of invention includes distilled water, deionized water (DI), water-for-injection (WFI) and/or low pyrogen water (LPW). WFI, which is preferred, is deionized, distilled water. The specific method of purifying water is not as important as the requirement that it needs to be low in endotoxin content.

The water and the reagents used in the present invention are substantially free from endotoxin contamination. Preferably, the water and the reagents used in the present invention are completely free from endotoxin contamination. One way to reduce the risk of endotoxin contamination can be to reduce the amount of water and reagent buffers exposed to the hemoglobin preparation. Therefore, under some embodiments of the present invention, the hemoglobin preparations are made using counter-flow or counter-current dialysis for equilibration of buffers and/or removal of reaction products. Counter flow dialysis methods are suitable for use in the present invention are commercially available e.g., VariPerm M, bitop, Witten (see, e.g., Schwarz, T. et al, *Electrophoresis* 15:1118-1119 (1994)), Spectrum Laboratories, Inc., Laguna Hills, Calif., etc. It is estimated that the hollow fiber technique may yield a hemoglobin preparation of the present invention that has a 100 fold reduction in the amount of endotoxin as compared to standard synthesis techniques. It is understood that other methods of removing the endotoxins are known in the art and are within the scope of the present invention.

In one method used to collect the erythrocytes, the blood samples can be washed several times with an isotonic solution and the plasma can be separated by centrifugation at 3,000 rpm in a 4" diameter bowl. Preferably, the isotonic solution used is a saline solution. Preferably, the cells are washed at least three times, rinsed between each centrifugation, and resuspended in a final volume of an equal volume of isotonic solution. Alternatively, concentration of RBCS may be accomplished by filtration over a tangential flow membrane.

The use of a sonicator may be discouraged as it makes membrane spheres (often referred to as "dust"). Agitation methods suitable for use in the present invention may include a magnetic stir bar (0.25" in diameter) and a mechanical rocker or shaker. (one to two liter container capacity may be used). This exemplary protocol describes equipment to illustrate the limitation of forces acting upon the collected cells to prevent undesirable fracturing of the cell membranes at this point.

It is understood that methods generally known in the art for separating RBCs from other blood components can be employed. For example, sedimentation, wherein the separation method does not rupture the cell membranes of a significant amount of the RBCs, such as less than about 30% of the RBCs, prior to RBC separation from the other blood components such as, white blood cells (WBCs) and platelets.

White blood cells can cause febrile reactions in human recipients when present in transfused packed RBCs. It is desirable to use a leucoreduction filter which can pass the RBCs but markedly reduce the number of WBCs. A larger prototype than that used for single human unit of packed cells is used to evaluate the leucoreduction. Prechilling washed bovine erythrocytes for about 12 h permits leukoreduction of filtration in about 15 minutes. The results are shown in Table 1. A 3 log reduction in WBCs, as quantified by instruments such as a Coulter Counter® Cell and Particle Counter is achieved by the passage of the red cell suspension through a leucocyte reduction filter. This is an alternative to the method wherein RBCs are selectively lysed in the presence of WBCs without lysing the WBCs, which are subsequently removed by filtration. This selective lysing is discussed more fully below.

TABLE 1

Leucocyte Reduction Filter

| Sample | Initial WBC/mm$^3$ | Vol Adjusted Final WBC/mm$^3$ | % Removal | Log$_{10}$ Removal |
|---|---|---|---|---|
| 12 h Cold Bovine | 6.13 × 10$^3$ | 28 | 99.6% | 3 |

Figure 2:
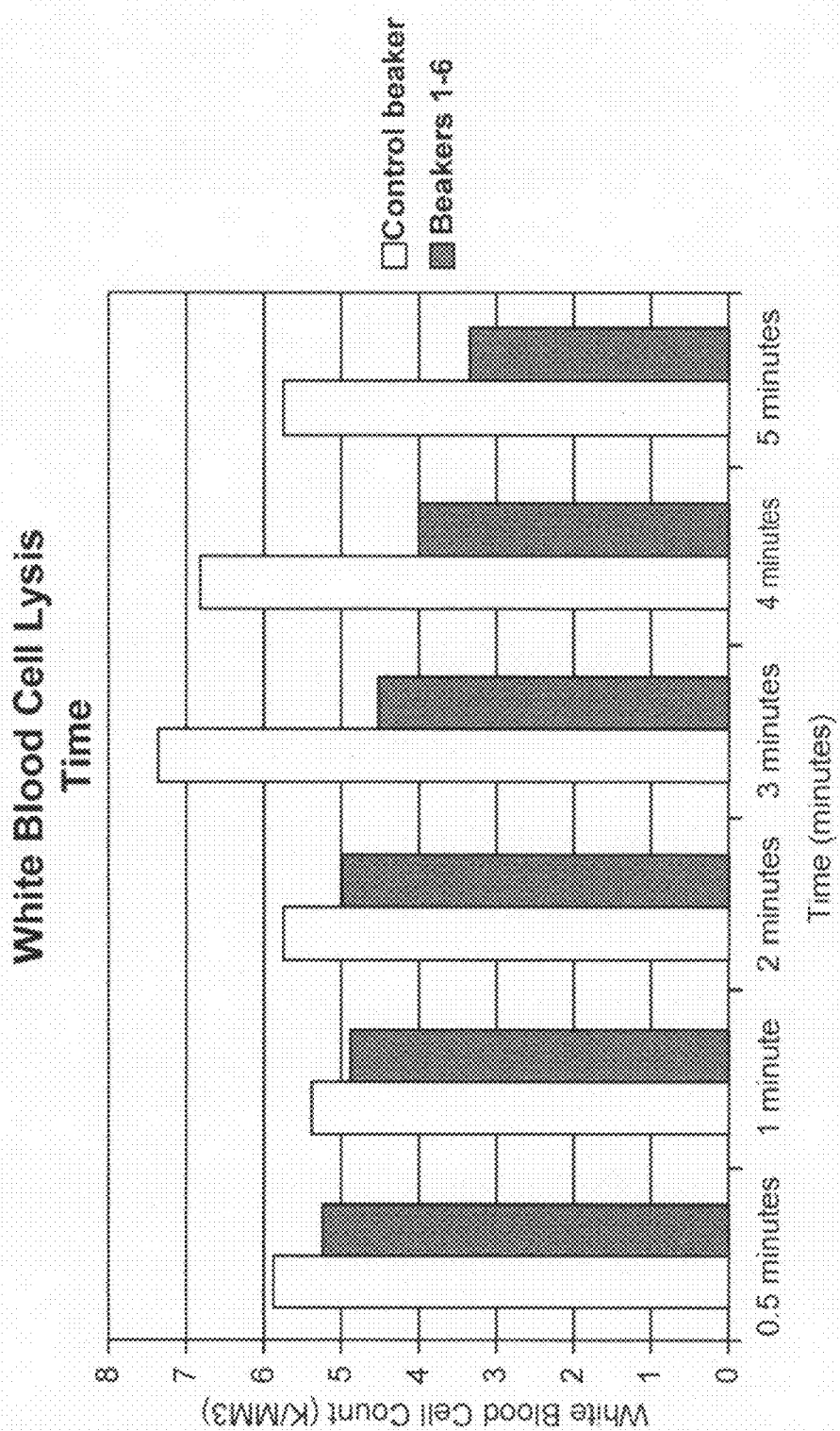
FIG. 2 depicts the time course of a lysis experiment showing resistance of WBC lysis.

3. Step 102. Lysis of Erythrocytes. Various lysis methods can be used, such as mechanical lysis, chemical lysis, hypotonic lysis or other known lysis methods which release hemoglobin without significantly damaging the ability of the Hb to transport and release oxygen. Hemoglobin may be released from the erythrocyte by hypotonic lysis in deionized water. Preferably, lysis is accomplished in four to twenty volumes of deionized water. In one method, plasma free blood cells are equilibrated with NS, and then diluted into 4 volumes of deionized water (DI). This can result in the fracturing of the plasma free blood cells by the hypotonic lysis. The cells are fractured by the rapid uptake of water. Red blood cells can be lysed in about 30 seconds, while WBCs are more resistant. RBCs are collected in a flow process after the RBCs are allowed to lyse but just before the WBCs begin to lyse, an additional volume of a 9% saline solution is added to arrive at a total concentration of 0.9% saline content overall. This timed increase in salinity prevents WBCs from lysing. The stroma and WBCs are removed from the lysed RBCs by filtration. The hemoglobin can then be removed by a 0.22 µm filter as filtrate while the retentate would concentrate the stroma, red cell membranes, and the unlysed WBCs. FIG. 2 depicts the time course of a lysis experiment showing resistance of WBC lysis for up to 5 minutes. Erythrocyte lysis can be stopped during the two minute period before appreciable leucocyte lysis occurs.

Other methods of erythrocyte lysis, such as "slow hypotonic lysis" or "freeze thaw", may also be employed. See, e.g., Chan et al., *J. Cell Physiol.* 85:47-57 (1975), incorporated by reference in its entirety. In some embodiments of the present invention, the cells are lysed by flow mixing red blood cells in isotonic saline with 12 volumes of deionized, endotoxin-free water and subjecting the cells to gentle agitation. It is understood that other methods of lysing the RBCs are known in the art and are within the scope of the present invention.

4. Step 103. Separation of Stroma from Hemoglobin. The contents of the erythrocyte are about 98.5% in pure hemoglobin, with some small amount of other proteins including carbonic anhydrase. The membranes of red blood cells are referred to as ghosts or stroma and contain all of the blood type antigens. Rabiner et al. first demonstrated that some of the toxic properties of hemolyzed red blood cells were related to the membrane (stroma) of red blood cells and their related lipids (Rabiner et al., *J. Exp. Med.* 126:1127 (1967), incorporated by reference in its entirety). The membranes can be destroyed by freezing so that storage requirements for blood may require climate controlled refrigeration. In addition, many of the human viral diseases transmitted through blood transfusions may adhere to the stroma of red blood cells. Thus, stroma-free hemoglobin ("SFH") can be beneficial in light of the immunogenic properties, such as inflammation, agglutination, clotting, an immune mediated complement response, platelet activation, etc, of the cell membranes of red blood cells, and possibility of viral contamination.

An effective stroma-free hemoglobin blood substitute or oxygen delivery therapy can offer several advantages over conventional blood based therapies. Significantly, the use of stroma-free hemoglobin blood substitutes can reduce the extent and severity of undesired immune responses, and the risk of transmission of viral diseases, including hepatitis and HIV. Moreover, in contrast to the limited storage capacity of erythrocytes, a stroma-free hemoglobin blood substitute or oxygen delivery therapeutic can exhibit an extended shelf life, and require less rigorous environmentally controlled storage facilities.

The stroma may be removed by ultrafiltration of the hemolysate over a 0.65 micron filter which retains the cellular components and passes the hemoglobin. Alternatively, the cellular debris may be removed by subsequent filtration through a 0.22 micron filter or a 300,000 Dalton molecular weight filter. Ultrafiltration membranes suitable for use in the present invention are commercially available from, for example, Millipore Corporation. Other methods for separating Hb from the lysed RBC phase can be employed, including sedimentation, precipitation (Tye, U.S. Pat. No. 4,529,719), centrifugation or microfiltration. It is understood that other methods of removing stroma are known in the art and are within the scope of the present invention.

Carbonic Anhydrase. Carbonic anhydrase will be removed through diafiltration once the red cell membrane has been lysed, which is employed at several points in this method. For example, diafiltration and buffer exchanges occur before, during and after cross-linking. The presence of carbonic anhydrase may be quantified by ELISA.

Microscopic analysis of 10 ml spun samples does not reveal any cellular debris.

Phospholipid Level Reduction. Another key element to the stable NO-blocked tetrameric hemoglobins of the invention is the low level of phospholipids present. Phospholipids derive from the surface lipid layer of the red cells, the source of the hemoglobin. The steps of processing given above remove these unwanted lipids, thus eliminating the problems associated with their presence. Phospholipid assays can be measured by HPLC and/or ELISA as is well known to one skilled in the art. Phosphatidylcholine is found to be below the limit of detection.

Concentration of Hemoglobin to 14% Solution. After such treatment, the stroma-free hemolysate is concentrated by a membrane that does not allow for the passage of hemoglobin. Preferably, the stroma-free hemolysate is concentrated using a filter having a 10,000 MW cut-off. Preferably, the stroma-free hemolysate is concentrated to a 1%-25% (g/l) solution. More preferably, the stroma-free hemolysate is concentrated to about 5% to about 20%. Most preferably, the stroma-free hemolysate is concentrated to about 6% to about 10%. The concentrated solution can be equilibrated with buffer and the pH is adjusted. Preferably, the pH is adjusted to a pH of 7.40. However, a pH of between about 6.5 and about 8.5 can be used in the present invention.

Optionally, the concentrated Hb solution can then be directed into one or more parallel chromatographic columns to further separate the hemoglobin by high performance liquid chromatography from other contaminants such as antibodies, endotoxins, phospholipids and enzymes and viruses. Examples of suitable media include anion exchange media, cation exchange media, hydrophobic interaction media and affinity media. The chromatographic columns may contain an anion exchange medium suitable to separate Hb from non-hemoglobin proteins. Suitable anion exchange mediums include, for example, silica, alumina, titanium gel, cross-linked dextran, agarose or a derivatized moiety, such as a polyacrylamide, a polyhydroxyethyl-methacrylate or a styrene divinylbenzene, that has been derivatized with a cationic chemical functionality, such as a diethylaminoethyl or quaternary aminoethyl group. A suitable anion exchange medium and corresponding eluents for the selective absorption and desorption of Hb as compared to other proteins and contaminants, which are likely to be in a lysed RBC phase, are readily determinable by one of reasonable skill in the art.

Removal of Phosphate Ion. Bucci et al. (U.S. Pat. No. 5,290,919) have reported that removal of organic phosphates, e.g., 2,3-diphosphoglycerate, may be necessary in human hemolysates because the site of the cross-linking reaction is the same as that occupied by 2,3-diphosphoglycerate in hemoglobin. In some embodiments of the present invention, the stroma free human Hb solution is substantially free from inorganic phosphate. Accordingly, in some embodiments of the present invention, the stroma free human Hb (before cross linking) that has passed through the filter may be then treated to exchange phosphate for chloride. For this purpose, the stroma free human Hb can be passed in the absence or presence of oxygen, through an ion exchange column that has been previously prepared and equilibrated with chloride. Efficacy of this step may be measured by total inorganic phosphate analysis. Suitable ionic resins are commercially available and are within the scope of the present invention. The ionic resin removes phosphate that may compete for the site to which aspirin binds during the reaction with DBSF. The solution can then be concentrated to the desired range. This operation is not necessary when using bovine Hb.

5. Step 104. Removal of Oxygen. The thiol blocked stroma free Hb or more specifically, the CMSFH can be treated under conditions sufficient to remove oxygen present in the preparation. One aspect of the present invention concerns an improved process for removing oxygen from CMSFH preparations. Without limiting the scope of the present invention, such deoxygenation can be carried out before or after any of the steps disclosed herein. For example, the deoxygenation step can be performed prior to or after the step of removing stroma, the step of removing the endotoxins, the step of thiol protection, the step of phosphate removal, the step of lysis of RBCs, or the step of cross-linking of the hemoglobin. In one embodiment, such deoxygenation is performed prior to the protection of the thiol group in the cysteine moiety of the hemoglobin of the present invention. In another embodiment of the invention, deoxygenation is performed prior to cross linking the hemoglobin. In some embodiments of the invention, the steps of the method may require more time to be completed. In such cases, deoxygenated conditions may be preferred.

The extent of deoxygenation can be measured by gas chromatograph, zirconium-based detector (e.g., a "MOCON" analyzer (Mocon, Minneapolis, Minn.), by measuring $pO_2$ or by measuring the spectral shift that is characteristic of deoxy-hemoglobin formation.

Oxygen in the hemoglobin can be removed by vacuum, or by vacuum centrifugation. The CMSFH used may be an ultrafiltrate obtained from the removal of stroma (dilute) or a retentate from the ultrafiltration of the second stage ultrafiltration conducted to concentrate the hemoglobin to approximately 10% (w/v). Either of these solutions of CMSFH obtained can be readily deoxygenated by applying a vacuum sufficient to equal the partial pressure of water at the temperature of the solution, while the solution can be centrifuged at a speed sufficient to produce a force greater than the surface tension of the solution. These are generally low speeds and can be met with preparatory centrifuges, or those of a continuous flow variety. It may be desirable to consider the geometry of the containers of the CMSFH to insure that there may be adequate surface area for gas exchange and that the temperature can be maintained and the solution not allowed to freeze.

Contactor membrane technology can be used to remove $O_2$ from Hb solutions. The contactor membrane technology can also be used for oxygenation where oxygen gas may be used instead of nitrogen gas. Three or four of such membranes may be attached in series for higher throughput and can be used for commercial production of deoxygenated or oxygenated hemoglobin solution. The Hb concentration affects the rate at which the dissolved $O_2$ is removed. As the Hb concentration is lowered the $O_2$ removal rate increases. The experiment may not lower $O_2$ concentration to <100 ppb. However, the test can be performed in the anaerobic glove box to make the system gas tight. The glove box can maintain the environment at very low $O_2$ levels (<5 ppb). This glove box environment can provide the $O_2$ barrier required to ensure that no $O_2$ can be re-absorbed by the Hb. Hg vacuum greater than 28.5" (<50 mm Hg) can be used for optimum $O_2$ removal.

The deoxygenated, endotoxin free, stroma free, carboxamidomethylated Hb (dCMSFH) prepared in the manner described above may be preferably maintained in an inert environment and the pH of the preparation may be preferably adjusted to a range between 6.0 and 9.5, and most preferably about pH 8.3-8.4. The pH of the solution may be adjusted using 1.0 N acetic acid or 1.0 N NaOH. Where dilution, suspension, or addition of water (including buffers, etc.) for other purposes is desired, such water may be deoxygenated and be free of endotoxin. All subsequent steps may be carried out in the absence of oxygen, maintained by what ever means is desired. As indicated above, a preferred method involves the use of nitrogen positive pressure environmental glove box, however, other inert gases (e.g., argon) may be equivalently employed in lieu of nitrogen.

6. Step 105. Protecting the Sulfhydryl of the Cysteine(s) of the Hemoglobin. The step of protecting cysteine of the hemoglobin with thiol protecting groups may be carried out before the cross linking step or after the cross linking step. In one embodiment of the present invention, the step of protecting the thiol group in the cysteine moiety is carried out before the cross-linking step. In another embodiment of the present invention, the step of deoxygenating the hemoglobin is carried out before the step of protecting the thiol group in the cysteine moiety. In some embodiments of the invention, deoxygenation is not performed prior to protecting the sulfhydryl groups in the hemoglobin. All the reagents known in the art for the protection of a functional group such as, but not limited to, hydroxyl, thiol, or carboxyl, are included in the present invention.

Some of the examples of the reagents include, but are not limited to, 4-pyridylmethyl chloride, alkoxyalkylchloride, dimethoxymethane, N-(hydroxymethyl)acetamide, triphenylmethyl chloride, acetyl chloride, 2-chloroacetic acid, acetic anhydride, haloacetamide such as, iodoacetamide, bromoacetamide, chloroacetamide, or fluoroacetamide, haloacetate such as iodoacetate, bromoacetate, chloroacetate, or fluoroacetate, benzyl chloride, benzoyl chloride, di-tert-butyl dicarbonate, p-hydroxyphenacyl bromide, p-acetoxybenzyl chloride, p-methoxybenzyl chloride, 2,4-dinitrophenyl fluoride, tetrahydropyran, acetamidohydroxymethane, acetone, bis-carboethoxyethene, 2,2,2-trichloroethoxycarbonyl chloride, tert-butoxycarbonyl chloride, alkyl isocyanate, and alkoxyalkyl isocyanate. In a specific example of the sulfhydryl protected hemoglobins of the invention, the reagent is iodoacetamide. It is understood that any reagent known in the art that can be used for carboxamidomethylation.

Optimization of the Reaction with iodoacetamide (IAM): The iodoacetamide reaction is followed with an iodide specific electrode, since one of the byproducts is iodide ion. A two molar excess per equivalent of sulfhydryl group can be used. Table 2 shows a grid of time course of the iodoacetamide reaction for bovine Hb vs. the moles of IAM reagent used in the IAM reaction. The results show the amount of free sulfhydryl per mole of Hb and are given in units of molar equivalents relative to bovine Hb.

TABLE 2

Reaction of Bovine Hb with IAM. Results given in equivalents of free sulfhydryl remaining.

| Moles IAM | Time | | | | | | |
|---|---|---|---|---|---|---|---|
| | 0 | 15 | 30 | 45 | 60 | 75 | 90 | 120 |
| 2 | 2 | 1.0 | 0.5 | 0.5 | | | | |
| 4 | | | | | 0.5 | 0.2 | 0.1 | <0.1 |

7. Step 106. Separating Thiol-Protected Hemoglobin from reactants. After the reaction is complete, as determined by the rate of iodide evolution observed, excess IAM is removed by equilibration with Ringer's Acetate and diafiltration.

8. Step 107. Cross-Linking with DBSF and Reaction with PLP. Stroma-free Hb can be prevented from dissociation into α,β dimers by cross-linking intramolecularly to prevent dissociation of the tetramer into α,β dimers and thus increase its circulatory half-life. This restricts Hb into the T state and resultantly can modify the affinity for oxygen and therefore modifies the oxygen transport properties of the Hb.

Examples of suitable cross-linking agents include polyfunctional agents that will cross-link Hb proteins, such as glutaraldehyde, succindialdehyde, activated forms of polyoxyethylene and dextran, α-hydroxy aldehydes, such as glycolaldehyde, N-maleimido-6-aminocaproyl-(2'-nitro,4'-sulfonic acid)-phenyl ester, m-maleimidobenzoic acid-N-hydroxysuccinimide ester, succinimidyl 4-(N-maleimidomethyl)cyclohexane-1-carboxylate, sulfosuccinimidyl 4-(N-maleimidomethyl)cyclohexane-1-carboxylate, m-maleimidobenzoyl-N-hydroxysuccinimide ester, m-maleimidobenzoyl-N-hydroxysulfosuccinimide ester, N-succinimidyl(4-iodoacetyl)aminobenzoate, sulfosuccinimidyl(4-iodoacetyl)aminobenzoate, succinimidyl 4-(p-maleimidophenyl)butyrate, sulfosuccinimidyl 4-(p-maleimidophenyl)butyrate, 1-ethyl-3-(3-dimethylaminopropyl) carbodiimide hydrochloride, N,N'-phenylene dimaleimide, and compounds belonging to the bis-imidate class, the acyl diazide class or the aryl dihalide class, among others. The saccharides can be used as cross-linking agents. The examples of saccharides include, but are not limited to, monosaccharides (galactose, glucose, methylglucopyranoside, and mannitol), disaccharides (lactose, maltose, cellobiose, sucrose, and trehalose), a trisaccharide (raffinose) and polysaccharides (dextrans with molecular weights of 15,000 and 71,000 Da).

The cross-linking of hemoglobin may be conducted in the absence of oxygen. Inorganic phosphate, which binds tightly to the hemoglobin molecule and interferes with the cross-linking reaction, may be removed to increase yield. Endotoxins, which bind tightly to the hemoglobin molecule and become a hepatic toxin when the hemoglobin is metabolized, may not be allowed to contact the hemoglobin.

A suitable amount of a cross-linking agent may be that amount which may permit intramolecular cross-linking to stabilize the Hb and also intermolecular cross-linking to form polymers of Hb, to thereby increase intravascular retention. Without limiting the scope of the present invention, various strategies can be employed to cross-link Hb with desirable molecular weight distributions and oxygen binding properties. The type and concentration of both cross linking and quenching agents, the duration of the cross-linking/polymerization reaction, and utilization of reducing agents are all possible variables that can be modified in these reactions to engineer the molecular weight distribution, oxygen binding properties, and metHb levels of cross-linked Hb dispersions.

Optimization of cross linking using pH control and excess cross linking agent: Table 3 shows a grid of increasing pH vs. mole ratio of cross linking agent (DBSF) over 2 h. The results show the percentage of alpha chain left unreacted at different pH and equivalents (in moles) DBSF at the end of the 2 h period. The pH is maintained constant with titration of the acid produced by reaction with NaOH. After 2 h, the production of acid has long since ceased. Results of cross linking are determined using gel electrophoretic separations, looking for residual uncross linked alpha chains. In the standard method of production of the stable NO blocked tetrameric hemoglobins of the present invention, using 2 equivalents of DBSF, better than 98% cross-linking is achieved.

TABLE 3 pH vs. Molar Ratio DBSF. Percentage of Uncross-Linked Hemoglobin Remaining.

| Equivalents DBSF | pH | | | | |
|---|---|---|---|---|---|
| | 7 | 7.5 | 8 | 8.2 | 8.4 |
| 1 | | | | | 21% |
| 1.2 | | | | | 19% |
| 1.5 | | | | | 3% |
| 2.0 | 38% | 11% | 2.5% | 1.7% | 1.5% |
| 2.5 | | | | | 1.7% |

In some embodiments of the present invention, the dCMSFH is cross-linked with bis 3',5' dibromo salicyl fumarate (DBSF) (Tye, U.S. Pat. No. 4,529,719, hereby incorporated by reference in its entirety). DBSF cross-linker may be added with stirring to the dCMSFH preparation at a molar ratio of DBSF cross-linker: dCMSFH of greater than 1:1. Preferably, the molar ratio of DBSF cross-linker: dCMSFH is 2:1. Prior to such addition, the pH of the dCMSFH preparation is adjusted to 8.4 and maintained at 8.4 throughout the reaction. The pH of the reaction mixture is carefully maintained by the addition of acid or base since the solution is not buffered. The reaction is permitted to go to completion.

Figure 3:
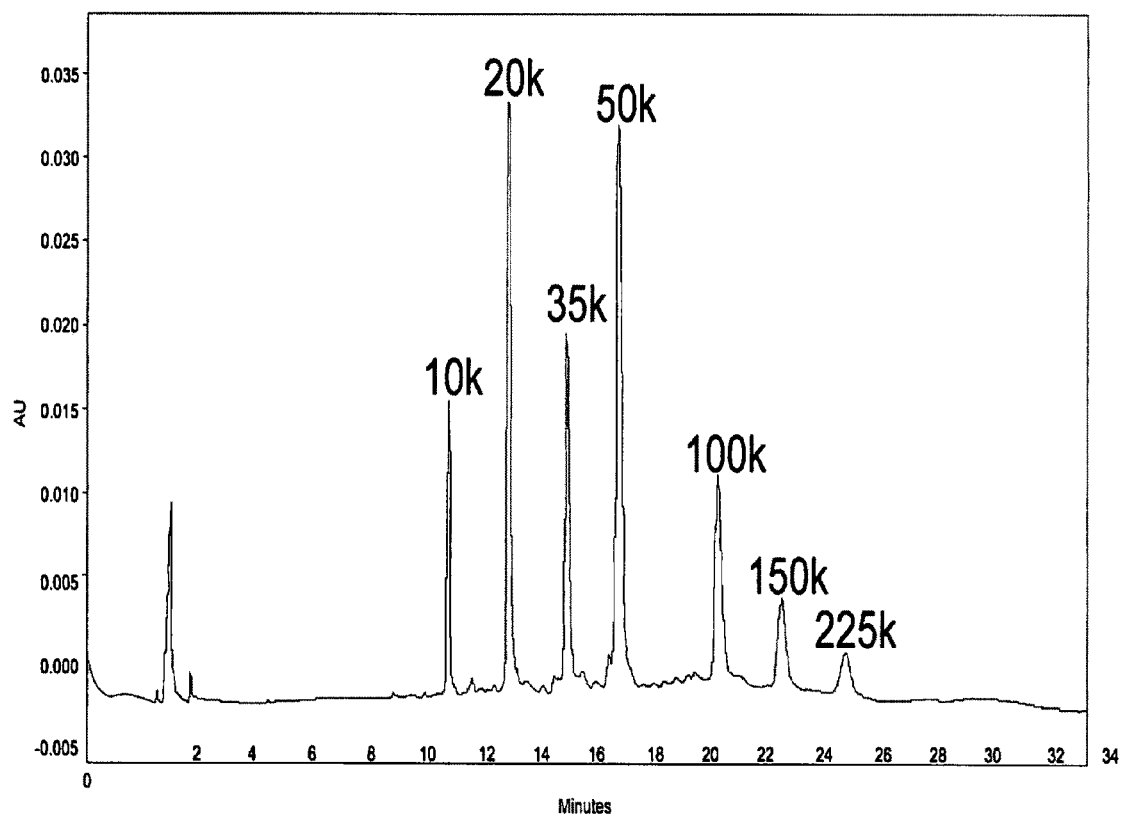
FIG. 3 depicts the size standards used in electrophoretic separations as disclosed within.

Determination of extent of cross linking using SDS gel electrophoresis: SDS can denature proteins to form long rods covered by negative charges of the carboxyl group at neutral pH. Proteins can then be separated by size exclusion using electrophoresis since the manifold excess of negative charge by the SDS can dwarf the charge heterogeneity of the native proteins. The Beckman Coulter PA-800® provides rapid record of the gel electrophoresis by using the absorption at 216 nm for the peptide bond. Standard protein mixtures can be used to calibrate the column for the range of molecular weights of interest, between 10 KDa and 100 KDa in the present case, as shown in FIG. 3.

Figure 4A:
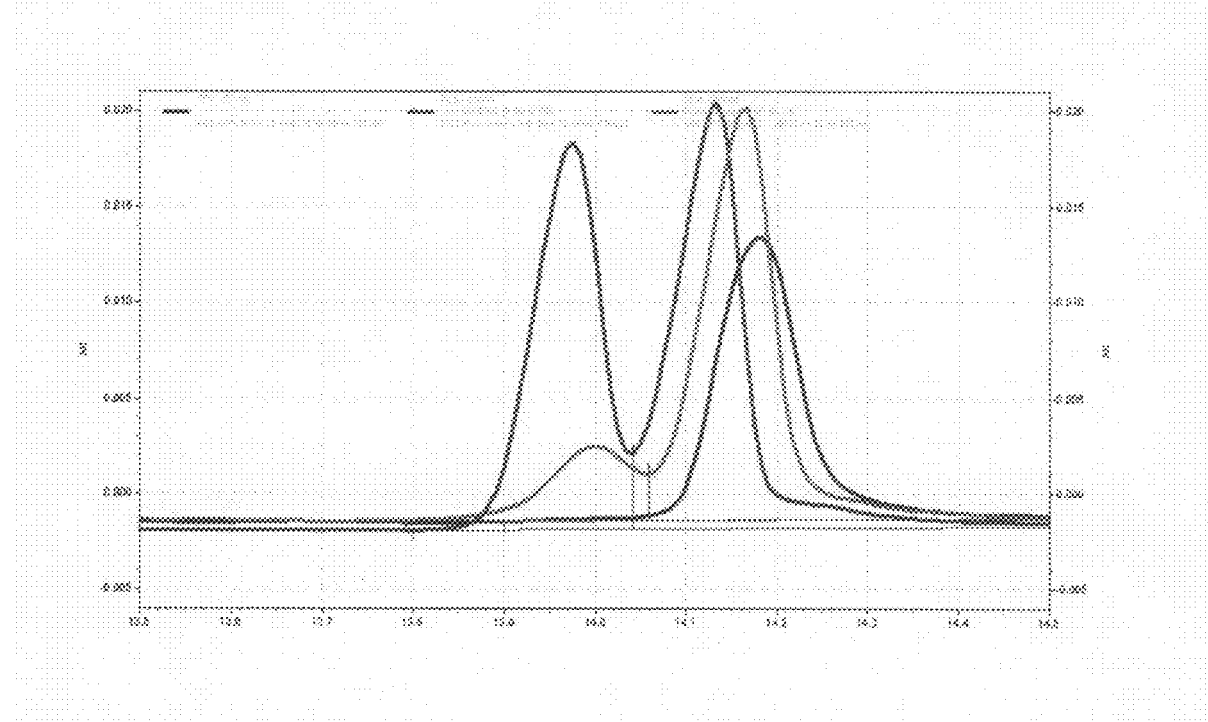
FIG. 4A depicts overlays of electrophoretic separations of native hemoglobin, dXCMSFH, and size standard in the range around 20 KDa.
Figure 7A:
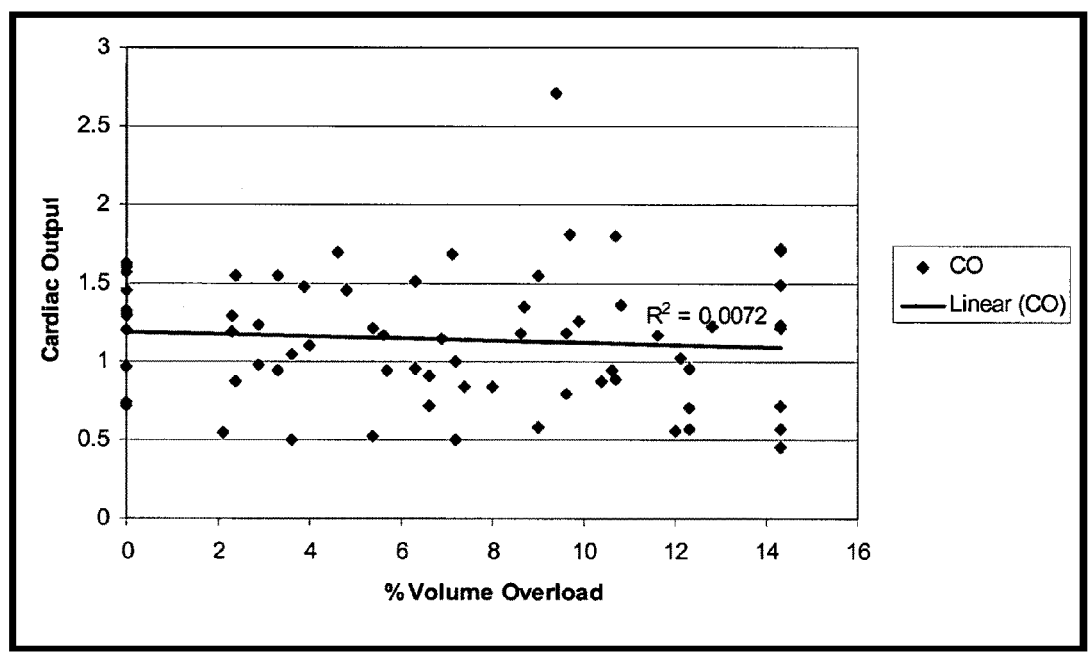
FIGS. 7A-D depict the cardiac output, systemic vascular resistance, and mean arterial pressure, respectively, in a pig safety trial.
Figure 7B:
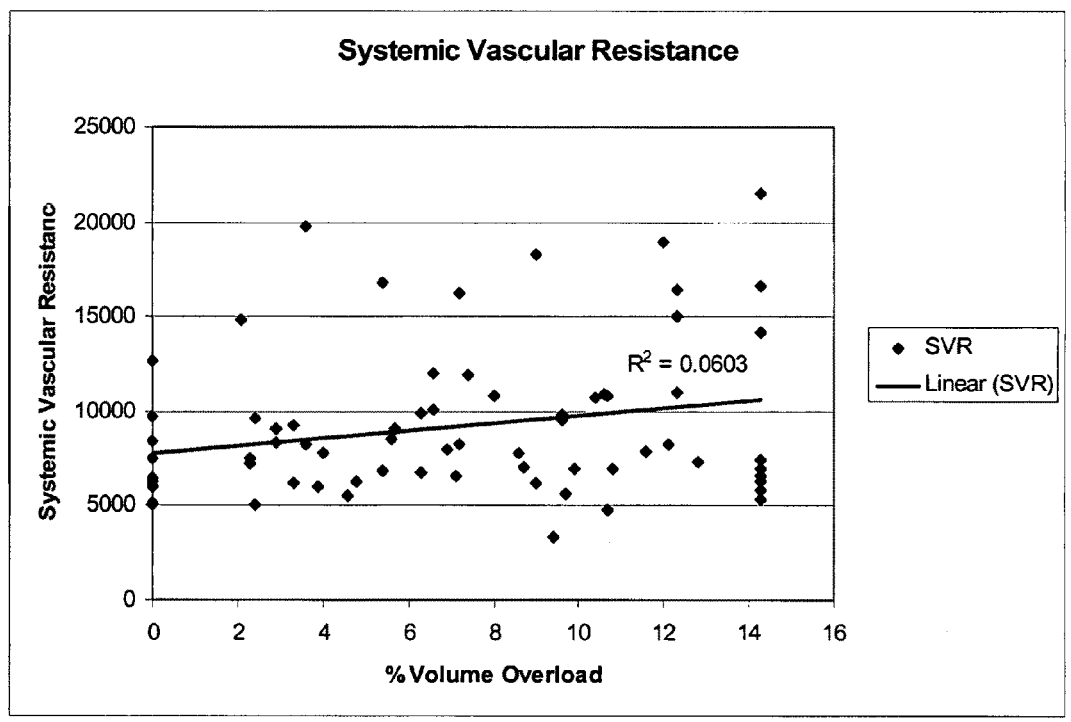
Figure 7C:
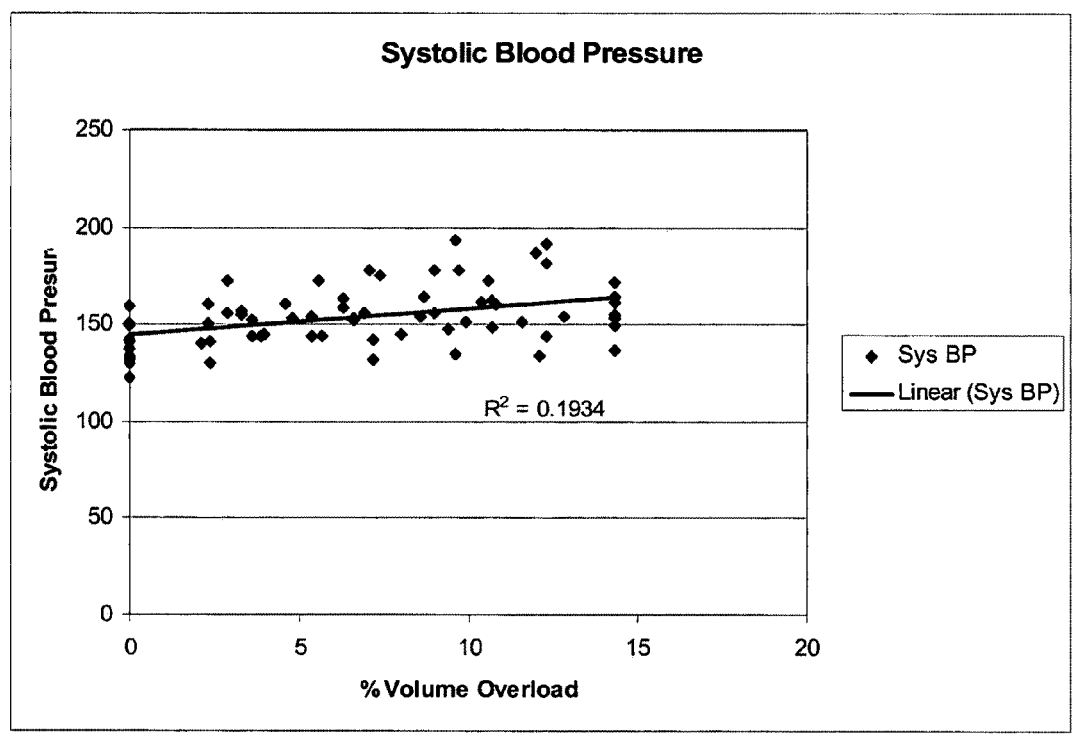
Figure 7D:
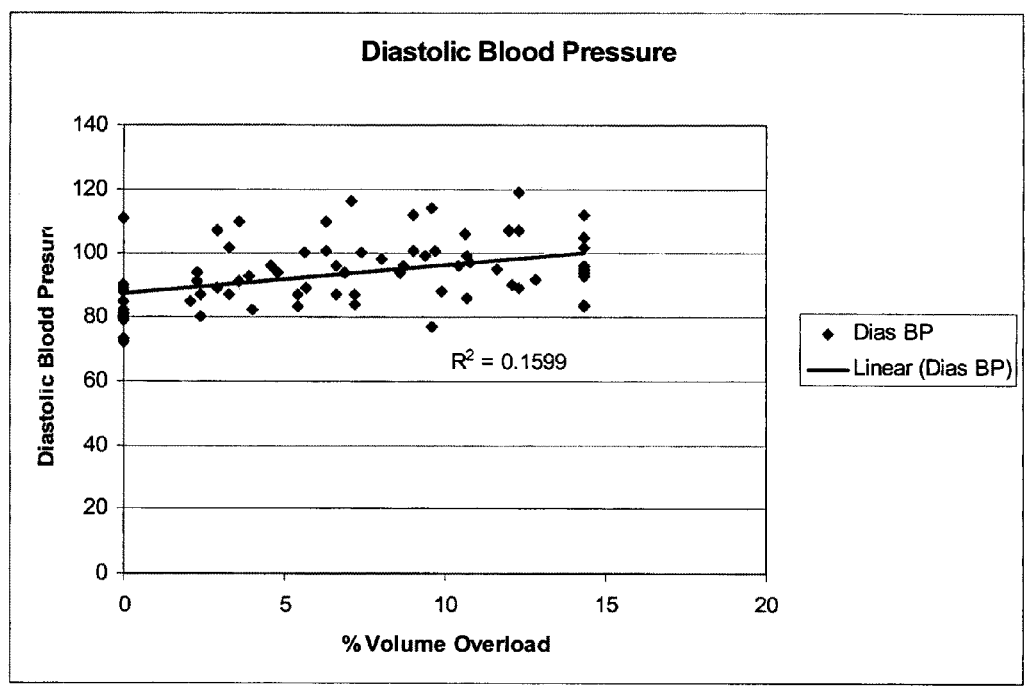

Native hemoglobin run on SDS gel electrophoresis can give two peaks with almost baseline separation between them. The first peak has been shown to be the alpha chain and the second the beta chain of hemoglobin. They can occur in almost equal amounts as there are equal numbers of chains in the molecule. This is illustrated in FIG. 4A, which is an expanded region of the overlaid electropherograms shown in FIG. 4B. Native hemoglobin appears as the green trace (rt13.98 and rt14.14), cross linked hemoglobin according to the present invention (dXCMSFH) appears as the red trace, and size standards are blue. The overlaid electropherograms shown in FIG. 4A are slightly offset for ease of viewing. The expanded region illustrated is clustered about the 20 KDa size standard, which is the region of interest for the two alpha and beta subunits of native hemoglobin. The experiment shown here for the cross-linked material is taken from a midpoint in the process, when most of the alpha chains have already cross linked, but significant amounts of beta chain still remain unreacted.

In FIG. 4B, the overlay of the full width electropherograms are shown, again with native hemoglobin in green, the cross linking experiment in red, and the size standards in blue. The fumaryl cross linking of the two alpha chains yields a pair of peptides tethered together and thus will appear at later elution times than the unreacted beta chains. The series of three new major product peaks at a higher molecular weight of about 36,000-45,000 KDA are seen in FIG. 4B at rt of 16 to 17 min. The product peaks may not be quantified as the size standards are all single peptide chains and cannot be extended for quantification for the dimerized products of this reaction. However, it can be seen that three higher molecular weight products are being formed.

There is a formation of β-β crosslink's in addition to the α-α crosslink's. There is a small amount of material at 90,000 KDa which can indicate the formation of a small number of inter molecular crosslink's.

Reaction of Human Hb with PLP. Pyridoxal-5-phosphate (PLP) has the ability to modify many hemoglobins. Although the properties of dXCMSFH from human hemoglobin benefit from the pyridoxal-5-phosphate reaction, dXCMSFH from bovine hemoglobin does not require this step. PLP modifies human hemoglobin by introducing a negative charge near a penultimate β chain histidine residue and by removing a positive charge at the amino terminal end of the same chain. These charge changes stabilize a new molecular configuration that is similar to the hemoglobin-DPG (diphosphoglycerate) complex. Significantly, the hemoglobin of this new configuration has an oxygen affinity resembling that of native hemoglobin within the red cell. The product may have one or two PLP molecules attached per tetramer. In prior PLP-hemoglobin preparations the intravascular retention time was too short to permit such preparations to be acceptable as a resuscitation fluid. Additionally, they were found to cause osmotic diuresis.

Accordingly, after the cross-linking reaction has been completed, where using human Hb, pyridoxal-5-phosphate (PLP) is added to the deoxygenated, endotoxin free, stroma free, carboxamidomethylated cross-linked human Hb (dXCMSFH) preparation. The PLP is reacted with the dXCMSFH and then reduced with sodium borohydride to form dXCMSFH-pyridoxal-5'-phosphate (dXCMSFH-PLP) using the methods described by Benesch et al. (Benesch et al., *Biochemistry* 11:3576 (1972) and references therein; Benesch et al. Proc. Natl. Acad Sci. 70 (9): 2595-9 (1974); Benesch et al., *Biochem. Biophys. Res. Commun.* 63(4): 1123-9 (1975); Benesch et al., *Methods Enzymol.* 76:147-59 (1981); Benesch et al., *J. Biol. Chem.* 257(3):13204 (1982); Schnackerz et al.; and, *J. Biol. Chem.* 258(2):872-5 (1983), all of which references are incorporated herein by reference in their entirety) with the change that all reagents are free of endotoxin and oxygen and the reaction occurs in the absence of oxygen. This treatment is not necessary when using bovine Hb Determination of Residual Uncross-linked Hemoglobin. High performance liquid chromatography (HPLC) Size Exclusion Chromatography (SEC) can be used to determine the percent of total cross-linked Hb, percent of cross-linked tetramer, or percent of cross linked higher order species of Hb/polyHb dispersions. A salt such as, $MgCl_2$ can serve to dissociate any non-cross-linked tetrameric Hb into α-β dimers, while cross-linked tetrameric Hb may remain intact. Hence, non-cross-linked Hb may elute in a separate peak away from intramolecularly cross-linked Hb.

Size exclusion HPLC on a Biorad Bio-Sil® SEC-12.5-5 column of the reaction mixture using 0.5M $MgCl_2$ solution as a buffer under conditions that would otherwise not denature the hemoglobin secondary structure, may be used to examine the amount of unreacted material, since under these conditions the equilibrium would favor the alpha beta dimer with a molecular weight of 32 KDa, which would be expected at greater retention times than seen for any peak in this experiment. As seen in FIG. 5, the HPLC trace shows the major peak at 64 KDa, with a minor peak at 128 KDa. There is no material at later elution times, and hence no materials with lower molecular weight. This experiment demonstrates the complete absence of unreacted hemoglobin and illustrates that most of the material is the stabilized tetramer of Hb with a molecular weight of 64 KDa.

9. Step 108. Preparing hemoglobin solutions by equilibration. The deoxygenated stable NO blocked tetrameric Hb and, in particular, dXCMSFH can be equilibrated with Ringer's lactate or Ringer's acetate solution, which under conditions of diafiltration, removes excess DBSF and byproducts of the reaction, for example, dibromosalicylic acid. Preferably, any ion removal or buffer equilibration can be performed using counter flow dialysis so as to prevent accumulation of endotoxin in the subsequent product. After equilibration, the solution can be sterile filtered into suitable infusion containers. Infusion containers suitable for use in the present invention may include, but are not limited to, sterile IV bags. Preferred infusion containers may prevent gas exchange (i.e., impermeable to oxygen) and the dXCMSFH can be stored in the absence of oxygen. This is expected to prevent heme oxidation which forms methemoglobin.

Determination of the Affinity for Oxygen by Modified Hemoglobin. Hemoglobin has an ability to bind and release oxygen under physiological conditions as a function of the partial pressure of oxygen in the system. Oxygen affinity of the hemoglobin derivative of the present invention can be measured using the Hemox-Analyzer (made by TCS Corporation or the gill cell described by Dolman et al., *Anal. Biochem.* 87:127 (1978), incorporated by reference in its entirety.

Hemox-Analyzer (made by TCS Corporation) allows the determination of the hemoglobin oxygen dissociation curve. Other methods to obtain a hemoglobin oxygen dissociation curve may not be as reproducible, accurate and easy to perform. The hemoglobin oxygen dissociation curves can be altered by changes in pH, temperature, $CO_2$ concentration, species of hemoglobin, variant of human hemoglobin, hemolyzed hemoglobin, and the like. The shape of the curve and the shift of the curve along the X axis can describe the ability of the hemoglobin to load and unload oxygen. The information can be useful in research for blood and modified hemoglobin as it is an in vitro test of in vivo function. It can measure the ability of hemoglobin to load and unload oxygen. A shorthand description of the entire hemoglobin dissociation curve can be given by the p50 for $O_2$, the partial pressure of oxygen in mm of Hg, which can cause the hemoglobin to be half saturated with oxygen.

Chemical modifications to hemoglobin or genetic variants to hemoglobin can cause the p50 to decrease, i.e. bind oxygen more tightly at any given oxygen pressure. In vivo this can mean less oxygen to perfused tissue.

The Hemox-Analyzer relies upon the change in color of blood (hemoglobin) that is arterial (oxygenated, red) and venous (less oxygenated, blue), and an oxygen electrode. A small dilute sample is prepared in a special spectrophotometric cell that has a small orifice in the bottom that allows a purified gas to be slowly bubbled through a stirred solution and also fitted with an oxygen electrode. The entire cell is precisely temperature controlled at 37° C., to equilibrate to body temperature. The outputs of the spectrophotometer and the oxygen electrode are analyzed and plotted. At the beginning of a plot the sample is fully oxygenated by bubbling pure oxygen through the sample until the oxygen saturation is greater than the fraction of oxygen in air (21%), then the gas bubbler is switched to nitrogen and the removal of oxygen begins. Oxygen equilibrium curves can thus be generated.

The p50 for human hemoglobin in RBCs can be about 28. The p50 falls to about 14 when RBCs are separated from the 2,3DPG which forms a salt bridge in the red cell to decrease the oxygen affinity. The p50 for bovine hemoglobin whether in the red cell or in free solution is about 25 to about 40 depending on the pH and the concentration of $CO_2$. FIG. 6 shows oxygen affinity curves for bovine whole blood, stroma free Hb, cross linked dXCMSFH of the invention, and fresh human blood. In the cross linked hemoglobin, the cross linking locks the hemoglobin in the tense state and therefore loses the sigmoidal curve. At lower $pO_2$, when $O_2$ is delivered to the tissues, the cross linked hemoglobin delivers more oxygen as compared to bovine whole blood, stroma free Hb, and fresh human blood. The p50 of cross linked hemoglobin is higher than that of human hemoglobin, and bovine hemoglobin. The p50 value for bovine whole blood is 24.73 mm Hg, for stroma free Hb is 21.20 mm Hg, for fresh human blood is 23.72 mm Hg and for dXCMSFH is 32.43 mm Hg, which is significantly higher than that of human RBCs. Therefore, the stable NO-blocked tetrameric Hb of present invention, and in particular, XCMSFH, may demonstrate greater efficiency to the delivery of oxygen per gram of hemoglobin. Although these numbers, as measured herein, are not identical to literature values (i.e., human blood p50 literature value is 27 mm Hg compared to 23.72 mm Hg reported here), the present values are a good relative measure of oxygen offloading performance.

The deoxygenated, endotoxin free, stroma free, carboxamidomethylated cross-linked Hb (dXCMSFH) of the present invention is a stabilized tetramer of bovine hemoglobin that is locked in the tense or T state, and has a p50 similar to hemoglobin within normal human red blood cells or, as shown in FIG. 6, higher. Thus, an equal amount of hemoglobin from a human red blood cell and hemoglobin from dXCMSFH, can carry the same amount of oxygen leaving the lung. However, dXCMSFH can deliver slightly more oxygen before its venous return, based upon the data shown in FIG. 6.

III. Analysis

1. Physical Characteristics of the Stable NO-Blocked Tetrameric Hemoglobins of the Invention A stable NO-blocked tetrameric hemoglobin of the present invention has a molecular weight distribution of about 65 kDa, a p50 of 20-45 mm Hg, an osmolality of 290-310 mOsm/Kg, with a pH of 6.0 to 7.9 at 10-22° C. The modified hemoglobins of the invention have a total hemoglobin of 6.0-20 g/dL, with methemoglobin levels of less than or equal to 5%, oxyhemoglobin levels of less than or equal to 10%. The modified hemoglobins of the invention have endotoxin levels of less than or equal to 0.02 EU/ml, phosphatidylcholine levels below detection limits, meet test for sterility, and a low level of extraneous organics. The modified hemoglobins of the present invention have a sodium ion level of 125-160 mmol/l, a potassium ion level of 3.5-5.5 mmol/l, a chloride ion level of 105-120 mmol/l, and a calcium level of 0.5-1.5 mmol/l. The modified hemoglobins of the invention have levels of N-acetyl cysteine of less than or equal to 0.22%.

2. Analytical Methods

Physical Chemical Analysis

The deoxygenated stable NO blocked tetrameric Hb and dXCMSFH, in particular, as disclosed herein can be analyzed at any step of the process of making it. Hemoglobin can be analyzed, for example, but not limited to, after removing stroma, after removing endotoxin, after lysis, after removing oxygen, after protection of thiol group in the cysteine moiety, or after cross-linking etc. The hemoglobin can be analyzed for purity, absorbance, structure, p50, nitric oxide binding capacity, white blood cell (WBC) count, microorganism growth in the hemoglobin solution, cross-linking, amino acid analysis, protein analysis, or effect of refrigeration or storage. Various analytical techniques are known in the art and are all within the scope of the present invention. Some of the examples of the analytical techniques are provided herein but they are not limiting to the scope of the present invention.

A. Mass Spectrometry (MS). There are many types of mass spectrometers and sample introduction techniques which allow a wide range of analyses and they are all included herein. In some preferred embodiments of the present invention, the technique used is mass spectrometry. Mass spectrometers may consist of three distinct regions: Ionizer, Ion Analyzer, and Detector. Ionization methods include, but are not limited to, electron impact (EI), chemical ionization (CI), electrospray (ESI), fast atom bombardment (FAB), and matrix assisted laser desorption (MALDI). Analyzers include but are not limited to, quadrupole, sector (magnetic and/or electrostatic), time-of-flight (TOF), and ion cyclotron resonance (ICR). Other related techniques are, for example, ion mobility spectrometry/mass spectrometry (IMS/MS), Tandem mass spectrometry (MS/MS), Orbitrap mass spectrometry. FTICR mass spectrometry, single-stage or a dual-stage reflectron (RETOF-MS, ladder sequencing with TOF-MS), Post-source decay with RETOF-MS MALDI, In-source decay with linear TOF-MS, and surface-enhanced laser desorption ionization-time of flight (SELDI-TOF). The mass spectrometer may be coupled with LC or GC.

B. UV-Vis. In some embodiments of the present invention, optical absorption spectroscopy (UV/VIS) has been used to determine the absorbance range for the hemoglobin. UV/VIS plays a role for the determination of concentrations of macromolecules such as proteins. Organic dyes can be used to enhance the absorption and to shift it into the visible range (e.g. Coomassie blue reagents). Understanding the forces that govern the interaction of proteins with one another assists in the understanding of such processes as macromolecular assembly, chaperone-assisted protein folding and protein translocation. Resonance Raman spectroscopy (RRS) is a tool which can be used to study molecular structure and dynamics. Resonance Raman scattering requires excitation within an electronic absorption band and results in a large increase of scattering. This approach may help to investigate specific parts of macromolecules by using different excitation wavelengths.

C. Liquid Chromatography (LC). Liquid chromatography is a tool for isolating proteins, peptides, and other molecules from complex mixtures. In some embodiments of the present invention, LC has been used for separation, purification and analysis of the hemoglobin and excipients used in the formulations of the invention. Examples of LC include affinity chromatography, gel filtration chromatography, anion exchange chromatography, cation exchange chromatography, diode array-LC and high performance liquid chromatography (HPLC) and affinity and size exclusion chromatography HPSEC.

Gel filtration chromatography and HPSEC chromatography separates proteins, and peptides on the basis of size. Gel Filtration Chromatography may be used for analysis of molecular size, for separations of components in a mixture, or for salt removal or buffer exchange from a preparation of macromolecules.

Affinity chromatography is the process of bioselective adsorption and subsequent recovery of a compound from an immobilized ligand.

Ion exchange chromatography separates molecules based on differences between the overall charges of the proteins. It is usually used for protein purification but may be used for purification of peptides, or other charged molecules. Elution can be achieved by increasing the ionic strength to break up the ionic interaction, or by changing the pH of the protein.

HPLC can be used in the separation, purification and detection of hemoglobin of the present invention. Use of reversed-phased chromatography (RPC) can be utilized in the process of protein structure determination. The normal procedure of this process can be 1) fragmentation by proteolysis or chemical cleavage; 2) purification; and 3) sequencing. A common mobile phase for RPC of peptides can be, for example, a gradient of 0.1% trifluoroacetic acid (TFA) in water to 0.1% TFA in a suitable organic solvent, such as acetonitrile, which provides for the solubilization of the proteins/peptides, permits detection at approximately 230-240 nmm, and is easily removable, i.e by evaporation, from the proteins/peptides.

The use of size-exclusion chromatography (SEC) and ion-exchange chromatography (IEC) can be used in determining the structure of the hemoglobin of the present invention. Full recovery of activity after exposure to the chromatography may be achieved, and SEC columns can allow fractionation from 10 to 1000 kilodaltons. The use of gradient elution with the IEC column may be favorable because of equivalent resolution as polyacrylamide gel electrophoresis (PAGE) and increased loading capability when compared to SEC. In liquid affinity chromatography (LAC) interaction may be based on binding of the protein due to mimicry of substrate, receptor, etc. The protein may be eluted by introducing a competitive binding agent or altering the protein configuration which may facilitate dissociation. HPLC may be coupled with MS.

D. Electrophoresis. Electrophoresis can be used for the analysis of the hemoglobin of the present invention. Electrophoresis can be gel electrophoresis or capillary electrophoresis.

Gel Electrophoresis: Gel electrophoresis is a technique that can be used for the separation of proteins. Separation of large (macro) molecules may depend upon two forces: charge and mass. During electrophoresis, macromolecules are forced to move through the pores when the electrical current is applied. Their rate of migration through the electric field depends on the strength of the field, size and shape of the molecules, relative hydrophobicity of the samples, and on the ionic strength and temperature of the buffer in which the molecules are moving. Using this technology it is possible to separate and identify protein molecules that differ by as little as a single amino acid. Also, gel electrophoresis allows determination of crucial properties of a protein such as its isoelectric point and approximate molecular weight. Electrofocusing or isoelectric focusing is a technique for separating different molecules by their electric charge differences, taking advantage of the fact that a molecule's charge changes as the pH of its surroundings changes.

Capillary Electrophoresis: Capillary electrophoresis is a collection of a range of separation techniques which may involve the application of high voltages across buffer filled capillaries to achieve separations. The variations include separation based on size and charge differences between analytes (termed capillary zone electrophoresis (CZE) or free solution CE (FSCE)), separation of neutral compounds using surfactant micelles (micellar electrokinetic capillary chromatography (MECC) or sometimes referred to as MEKC) sieving of solutes through a gel network (capillary gel electrophoresis, GCE), separation of cations (or anions) based on electrophoretic mobility (capillary isotachophoresis, CITP), and separation of zwitterionic solutes within a pH gradient (capillary isoelectric focusing, CIEF). Capillary electrochromatography (CEC) can be an associated electrokinetic separation technique which involves applying voltages across capillaries filled with silica gel stationary phases. Separation selectivity in CEC can be a combination of both electrophoretic and chromatographic processes. Many of the CE separation techniques rely on the presence of an electrically induced flow of solution (electroosmotic flow, EOF) within the capillary to pump solutes towards the detector. GCE and CIEF are of importance for the separation of biomolecules such as proteins.

E. Nuclear magnetic resonance (NMR). NMR can be used for the analysis of the hemoglobin of the present invention. NMR spectroscopy is capable of determining the structures of hemoglobin at atomic resolution. In addition, it is possible to study time dependent phenomena with NMR, such as intramolecular dynamics in macromolecules, reaction kinetics, molecular recognition or protein folding. Heteronuclei like $^{15}N$, $^{13}C$ and $^2H$, can be incorporated in proteins by uniformly or selective isotopic labeling. Spectra from these samples can be drastically simplified. Additionally, some new information about structure and dynamics of macromolecules can be determined with these methods.

F. X-ray crystallography. X-ray crystallography can be used for the analysis of the hemoglobin of the present invention. X-ray crystallography is a technique in which the pattern produced by the diffraction of X-rays through the closely spaced lattice of atoms in a crystal is recorded and then analyzed to reveal the nature of that lattice. This generally leads to an understanding of the material and molecular structure of a substance. The spacings in the crystal lattice can be determined by using Bragg's law. The electrons that surround the atoms, rather than the atomic nuclei themselves, are the entities which physically interact with the incoming X-ray photons. This technique can be used to determine the structure of the hemoglobin of the present invention. X-ray diffraction is commonly carried out using single crystals of a material, but if these are not available, microcrystalline powdered samples may also be used which may require different equipment.

G. Arrays. Arrays can be used for the analysis of the hemoglobin of the present invention. Arrays involve performing parallel analysis of multiple samples against known protein targets. The development of various microarray platforms can enable and accelerate the determination of protein abundance, localization, and interactions in a cell or tissue. Microarrays provide a platform that allows identification of protein interaction or function against a characterized set of proteins, antibodies, or peptides. Protein-based chips array proteins on a small surface and can directly measure the levels of proteins in tissues using fluorescence-based imaging. Proteins can be arrayed on either flat solid phases or in capillary systems (microfluidic arrays), and several different proteins can be applied to these arrays. Nonspecific protein stains can be then used to detect bound proteins.

H. Amino Acid Analysis. In some embodiments, amino acid analysis (AAA) is a technique used in the analysis of the hemoglobin of the present invention. AAA is a process to determine the quantities of each individual amino acid in a protein. There can be four steps in amino acid analysis: hydrolysis, derivatization, separation of derivatized amino acids, and data interpretation and calculations.

In the hydrolysis step, a known amount of internal standard (norleucine) may be added to the sample. The sample, containing at least 5 nmoles of each amino acid (i.e. 10 μg of protein) can be then transferred to a hydrolysis tube and dried under vacuum. The tube can be placed in a vial containing HCl and a small amount of phenol and the protein is hydrolyzed by the HCl vapors under vacuum. The hydrolysis is carried out for about 24 h at about 110° C. Following hydrolysis, the sample can be dried.

Derivatization can be performed automatically on the amino acid analyzer by reacting the free amino acids, under basic conditions, for example, with phenylisothiocyanate (PITC) to produce phenylthiocarbamyl (PTC) amino acid derivatives. A standard solution containing a known amount (500 pmol) of 17 common free amino acids can also be loaded on a separate amino acid analyzer sample spot and derivatized. This can be used to generate a calibration file that can be used to determine amino acid content of the sample. Following derivatization, a methanol solution containing the PTC-amino acids can be transferred to a narrow bore HPLC system using a reverse phase C18 silica column for separation. The buffer system used for separation can be for example, 50 mM sodium acetate at pH 5.45 as buffer A and 70% acetonitrile/32 mM sodium phosphate at pH 6.1 as buffer B. The program can be run using a gradient of buffer A and buffer B. Chromatographic peak areas can be identified and quantitated using a data analysis system that can be attached to the amino acid analyzer system.

Alternatively, the classical method of amino acid analysis of Moore and Stein using ninhydrin may be used.

Clinical Chemistry Analysis Methods

A. Oxygen transport. A CO-oximeter is used for comprehensive hemoglobin analysis to establish saturation, desaturation and methemoglobin levels. Ultraviolet illumination is used to for oxygen transport tests including levels of deoxyhemoglobin (HHb), oxyhemoglobin ($O_2$Hb), methemoglobin (MetHb), carboxyhemoglobin (COHb), total hemoglobin (tHb), oxygen saturation ($SO_2$ %), oxygen content ($O_2$Ct), and oxygen capacity ($O_2$Cap) in the hemoglobins of the invention. One suitable instrument is manufactured by Nova Biomedical Instrumentation.

B. Electrolytes. Electrolytes such as potassium, calcium, sodium chloride, and others are measured using standard electrolyte/chemistry analyzers. Suitable instrumentation is produced by Nova Biomedical, Hitachi, Roche, among others.

C. Osmolality. The osmolality of the hemoglobins of the invention is also measured. Freezing point depression is the methodology used to perform this analysis, in order to produce biocompatible volume expansion and oxygen delivery agents of the invention. Suitable instrumentation is available from Advanced Instruments Inc., and can measure all osmotically active solutes within the range of 0.0 to 4000 mOsmol/kgH$_2$O.

D. Carbonic anhydrase. Carbonic anhydrase may be detected by a double sandwich ELISA, wherein a polystryene support is coated with rabbit anti-bovine CA, to which CA in the samples will bind. The enzyme substrate reaction is quantified by visible absorbance of the products of the reaction.

E. Phospholipid Level Reduction. Phospholipid assays can be measured by HPLC and/or ELISA. The ELISA validation protocol is designed according to current USP guidelines for a Category II, quantitative assay to determine the presence of phosphatidylcholines. The protocol includes validation of linearity/range, accuracy and precision.

F. Assay for Endotoxin. The final product, ready for infusion, must be endotoxin free. Endotoxin is actually material from bacterial cell walls, and is responsible for initiation of a fever in the recipient, in low doses; while higher levels will initiate a more serious constellation of symptoms. The LAL (Limulus Ameobocyte Lysate) kinetic-turbidometric assay was chosen over other assays, such as the chromogenic and the gel-clot, because of its reproducible results and high degree of sensitivity.

The potency of Control Standard Endotoxin (CSE) used for routine testing is determined by comparison with Reference Standard Endotoxin (RSE), EC5, Lot F manufactured by the USPC. It is necessary to perform this comparison whenever an endotoxin other than the Referenced endotoxin is to be used for creating spikes and curves in routine testing. This is a consequence of the fact that different lots of CSE have markedly different potencies. The RSE/CSE comparison is performed by comparing one vial of RSE to four vials of the same lot of CSE and calculating an average potency. A standard curve is assayed in triplicate, with a coefficient of correlation of −0.98 or less required for qualification. Numerous CSE standard curves are run and one standard curve is archived for future testing. Inhibition/enhancement studies are performed on all products to be tested with the LAL assay. The LAL assay is performed using the protocol of Associates of Cape Cod, Falmouth Technology Park, East Falmouth Mass. 02536-4445, using a Pyros Kinetix® Incubating Tube Reader as manufactured by Associates of Cape Cod.

i. Reagent and Equipment Preparation

All reagents used for the kinetic-turbidometric assay are used according to the specific manufacturers' instructions with the following two exceptions: 1) the LAL is reconstituted with 5 ml of Pyrosol™ reconstitution buffer instead of LAL Reagent Water and 2) the CSE is not reconstituted with exactly 5 ml of LAL Reagent Water. The reconstitution of LAL with buffer is performed to overcome extreme enhancement of the LAL assay by pure hemoglobin solutions. The CSE is reconstituted with an amount of water which will yield a final solution concentration of 1000 EU/ml. The amount to be added is determined by standardizing the CSE against the USPC RSE and may be more or less than the 5 ml recommended by Associates of Cape Cod. This yields a constant CSE solution concentration and prevents recalculation of endotoxin spikes every time the CSE lot changes. All other reagents are used as directed.

All glassware is depyrogenated by heating to 180° C. for 4 h. All dilutions and solution transfers are performed under a class 100 laminar flow hood. All pipette tips used are sterile and pyrogen-free.

ii. Determination of CSE Potency

One vial of RSE (10,000 EU/vial by definition) was reconstituted with 5 ml of LAL Reagent Water to yield a 2,000 EU/ml solution. Two RSE curves were run to cover full range of current Q.C. testing. The mid-range curve contained the following concentrations (EU/ml): 1.0, 0.5, 0.25, 0.125, 0.0625, and 0.03125. The low range curve consisted of the following concentrations (EU/ml): 0.004, 0.002, 0.001, 0.0005, 0.00025, and 0.0001. These curves were run in duplicate, linear regression was performed to determine the slope and Y-intercept of the curves, and the curves were archived for the purpose of comparison with the CSE curves.

After the RSE curves had been run, 4 vials of CSE (500 ng/vial) were reconstituted with an amount of water which will yield a final solution concentration of 1000 EU/each. Dilutions of each vial were prepared in each of the two ranges so that at least three concentrations of the CSE curve would fall directly on the RSE curve. The mid-range curve contained the following concentrations (ng/ml): 0.1, 0.05, 0.025, 0.0125, 0.00625 and 0.003125. The low-range curve consisted of the following concentrations (ng/ml): 0.004, 0.002, 0.001, 0.0005, 0.00025, and 0.0001. These curves were run in duplicate and the onset times were interpolated off the corresponding RSE curve.

The endotoxin concentration in EU/ml for each CSE standard was divided by the corresponding concentration in ng/ml. Any onset times which did not fall directly on the RSE curve, indicated on the raw data by an asterisk, were not included in the calculations. The resulting EU/ng potencies for each standard were averaged to determine the CSE potency in each range. The two range potencies were then averaged to determine the potency of the CSE through the entire range of 1.0 to 0.001 EU/ml. The overall CSE potency was then used to calculate the amount of LAL Reagent Water to be added to each CSE Vial in the lot to yield a 1000 EU/ml solution according to the following calculations:

$$\frac{\frac{500 \text{ ng}}{\text{vial}}}{\frac{1000 \text{ } EU}{\text{ml}}} \times \frac{\text{potency } EU}{\text{ng}} = \frac{\text{water ml}}{\text{vial}}$$

iii. Test Method

100 µl of LAL is added to a depyrogenated 10×75 mm culture tube containing 400 µl of sample. The tube is vortexed gently for approximately 2 seconds and placed in the incubation module of the LAL device. Each tube is added individually in this manner. Timing is initiated for each tube as the bottom of the tube actuates a mechanical switch. Tubes are incubated at 37.0±0.5° C. throughout the test. No readings are taken for the first 60 this allows time for the contents of the tube to come to temperature and for air bubbles to disperse. For 60 to 120 seconds after tube insertion, photodetectors in each well take 7 readings 10 seconds apart. The readings are then averaged and taken to represent 100% transmittance. This zeroing period eliminates data errors due to tube imperfections and sample color or endogenous turbidity. Subsequent readings are taken every ten seconds, converted to transmittance, and then to optical density (OD). From 400 to 550 seconds, the OD values collected are averaged and then subtracted from all subsequent OD values for the test. (This baseline correction compensates for the OD of the background.)

Onset time, $T_o$, is defined as the number of seconds between placement of a sample in and incubating well and the development of an optical density of 20 mAU. The endotoxin level is determined by comparing the onset times to an archived standard curve of $\log_{10}(T_o)$ versus $\log_{10}$(known endotoxin concentration).

A small-programmed-computer is used to collect data from the LAL device. The LAL device software stores the OD values in data files and performs data analysis upon command such as onset time correction, linear regression on standards, and endotoxin concentration determination.

All in-process samples are tested in duplicate, unspiked and spiked, with a four-lambda spike, where lambda equals the lowest standard on the standard curve. In addition, a four-lambda spike in LAL Reagent Water and unspiked LAL Reagent Water are tested. All final product samples are tested unspiked and spiked, in triplicate.

Results. The levels of endotoxin in dXCMSFH are below 1 EU per/ml. In preferred embodiments of the process, the elimination of endotoxins to a level below 0.01 EU are achieved and allow for complex usage and for larger volumes. This results in readings of 0.1 EU per ml to below 0.02 EU per ml.

V. Formulations

1. Pharmaceutical Compositions Including Excipients, Routes of Administration and Dosages. The deoxygenated stable NO blocked tetrameric Hb, and dXCMSFH, in particular, of the present invention may be incorporated in conventional pharmaceutical formulations (e.g. injectable solutions) for use in treating mammals in need thereof. Pharmaceutical compositions can be administered by subcutaneous, intravenous, or intramuscular injection, or as large volume parenteral solutions and the like. In some embodiments, dXCMSFH of the present invention may be formulated by encapsulating Hb within liposomes. Liposome encapsulation is often used in drug delivery to reduce the toxicity of encapsulated therapeutic agents, as well as to increase drug half-life. The liposome-encapsulated hemoglobin (LEHb) encases Hb in a structure physiologically similar to RBCs, thus preventing Hb dissociation and its rapid clearance in the blood stream. The half-life of LEHb dispersions is dependent on the surface chemistry of the bilayer, as well as the bilayer surface charge and the vesicle size distribution. Hence, decreasing vesicle size and modifying the vesicle surface can significantly increase the circulatory lifetime. Surface conjugation of liposomes with polyethylene-glycol (PEG) can extend the half-life. The uptake of liposomes by the reticuloendothelial system (RES) affects the LEHb concentration that can be safely administered, since overloading the RES would impair the immune system.

The deoxygenated stable NO-blocked tetrameric Hb and, in particular, dXCMSFH of the present invention can also be formulated into other artificial blood and oxygen delivery therapeutic formulations. Such formulations can include other components in addition to the dXCMSFH. For example, a parenteral therapeutic composition can comprise a sterile isotonic saline solution. The formulations can be either in a form suitable for direct administration, or in a concentrated form requiring dilution prior to administration. The formulations of the present invention can thus contain between 0.001% and 90% (w/v) dXCMSFH. In some embodiments of the present invention, the extracellular hemoglobin solution of dXCMSFH of the present invention may contain from about 5 percent to about 20 percent, from about 5 percent to about 17 percent, from about 8 to about 14 percent, and about 10 percent hemoglobin in solution (% weight per volume). In some embodiments of the invention, the extracellular hemoglobin solution of dCMSFH may contain from about 5% to about 7% hemoglobin in solution (% w/v). In some embodiments of the invention the solution containing dCMSFH contains about 6.4% hemoglobin. The selection of percent hemoglobin depends on the oncotic properties of the chosen hemoglobin product. The hemoglobin solutions formulated for use in the present invention may be normo-oncontic to hyperoncotic. The percent hemoglobin may be adjusted to obtain the desired oncotic pressure for each indication.

dXCMSFH of the present invention can be used in compositions useful as blood substitutes and oxygen delivery therapeutics in any mammal that uses red blood cells for oxygen transport. The mammals include but are not limited to, human, livestock such as cattle, cat, horse, dog, sheep, goat, pig etc. In some embodiments of the invention, the mammal is human.

A dose of the dXCMSFH of the present invention can be from about 1 to about 15,000 milligrams of hemoglobin per kilogram of patient body weight over the appropriate time period either from initial dose or repeat dose. When used as an oxygen delivery composition, or as a blood volume supplement, the dosage may range between 100 to 7500 mg/kg patient body weight, 500 to 5000 mg/kg body weight, or 700 to 3000 mg/kg body weight. Thus, a dose for a human patient might be from a gram to over 1000 grams. It will be appreciated that the unit content of active ingredients contained in an individual dose of each dosage form need not in itself constitute an effective amount, as the necessary effective amount could be reached by administration of a number of individual doses. The selection of dosage depends upon the dosage form utilized, the condition being treated, and the particular purpose to be achieved according to the determination of those skilled in the art.

For use in the present invention, the deoxygenated stable NO blocked tetrameric HB and, in particular, the dXCMSFH of the present invention can be dialyzed or exchanged by ultrafiltration into a physiologically acceptable solution. The dXCMSFH of the present invention may be formulated at a concentration of 50-150 g/l. The solution may comprise a physiologically compatible electrolyte vehicle isosmotic with whole blood and which may maintain the reversible oxygen-carrying and delivery properties of the hemoglobin. The physiologically acceptable solution can be, for example, physiological saline, a saline-glucose mixture, Ringer's acetate, Ringer's solution, lactated Ringer's solution, Locke-Ringer's solution, Krebs-Ringer's solution, Hartmann's balanced saline, heparinized sodium citrate-citric acid-dextrose solution, and polymeric plasma substitutes, such as polyethylene oxide, polyvinyl pyrrolidone, polyvinyl alcohol and ethylene oxide-propylene glycol condensates.

Each formulation according to the present invention may additionally comprise inert constituents including pharmaceutically-acceptable carriers, diluents, fillers, salts, and other materials well-known in the art, the selection of which depends on the dosage form utilized, the condition being treated, the particular purpose to be achieved according to the determination of the ordinarily skilled artisan in the field and the properties of such additives. For example, the hemoglobin solution of the present invention in addition to dXCMSFH may include 0-200 mM of one or more physiological buffers, 0-200 mM of one or more carbohydrates, 0-200 mM of one or more alcohols or poly alcohols, 0-200 mM of one or more physiologically acceptable salts, and 0-1% of one or more surfactants, 0-20 mM of a reducing agent. The hemoglobin solution of the present invention in addition to dXCMSFH may include, 0-50 mM sodium gluconate, 0-50 mM of one or more carbohydrates (e.g. glucose, mannitol, sorbitol or others known to the art), 0-300 mM of one or more chloride salts and, optionally, 0-0.5% surfactant, e.g. Tween™ [polysorbate 80], and/or 0-20 mM N-acetyl cysteine.

Administration of the dXCMSFH of the present invention can occur for a period of seconds to hours depending on the purpose of the hemoglobin usage. For example, when used as an oxygen carrier for the treatment of severe hemorrhage, the usual time course of administration is as rapidly as possible. Typical infusion rates for hemoglobin solutions as volume enhancer or oxygen therapeutics can be, for example, from about 100 ml/h to about 3000 ml/h, from about 1 ml/kg/h to about 300 ml/kg/h, or from about 1 ml/kg/h to about 25 ml/kg/h. In some embodiments of the invention, the rates of administration may be higher.

Suitable compositions can also include 0-200 mM of one or more buffers (for example, acetate, phosphate, citrate, bicarbonate, or Goode's buffer). Salts such as sodium chloride, potassium chloride, sodium acetate, calcium chloride, magnesium chloride can also be included in the compositions of the invention. The salt can be in concentrations of 0-2M.

In addition, the compositions of the invention can include one or more carbohydrate (for example, reducing carbohydrates such as glucose, maltose, lactose or non-reducing carbohydrates such as sucrose, trehalose, raffinose, mannitol, isosucrose or stachyose) and one or more alcohol or poly alcohol (such as polyethylene glycols, propylene glycols, dextrans, or polyols). The concentration of carbohydrate or alcohol can be 0-2 M.

The dXCMSFH of the present invention can also contain one or more surfactant and 0-200 mM of one or more chelating agent (for example, ethylenediamine tetraacetic acid (EDTA), ethylene glycol-bis(beta-aminoethyl ether) N,N,N', N'-tetraacetic acid (EGTA), ophenanthroline, diethylamine triamine pentaacetic acid (DTPA also known as pentaacetic acid) and the like). The surfactant can be 0.005-1% of the composition. The compositions of the invention can be at pH of about 6.0-9.5. In some embodiments, the composition may contain 0-150 mM NaCl, 0-10 mM sodium phosphate, 0.01-0.1% surfactant, and/or 0-50 µM of one or more chelating agents at pH 6.0-9.5. The formulation may contain 5 mM sodium phosphate, 150 mM NaCl, 0.025% to 0.08% polysorbate 80, and/or 25 µM EDTA at pH 6.0-9.5.

Additional additives to the formulation can include antibacterial agent, oncotic pressure agent (e.g. albumin or polyethylene glycols) and other formulation acceptable salt, sugar and other excipients known in the art. Each formulation according to the present invention can additionally comprise constituents including carriers, diluents, fillers, salts, and other materials well-known in the art, the selection of which depends upon the particular purpose to be achieved and the properties of such additives which can be readily determined by one skilled in the art. The compositions of the present invention can be formulated by any method known in the art. Such formulation methods include, for example, simple mixing, sequential addition, emulsification, diafiltration and the like.

2. Packaging and Storage of The NO-Blocked Tetrameric Hb of the Invention, Including Both Stable (Cross linked) and Unstabilized (Uncross linked) Hb. Various embodiments of the NO-blocked tetrameric Hb of the invention, including dXCMSFH, dCMSFH, and dTBSFH may be stored in conventional, and preferably oxygen impermeable containers (for example, stainless steel tanks, glass containers, oxygen impermeable plastic bags, or plastic bags overwrapped with low oxygen permeable plastic bags wherein an oxygen scavenger is placed between the internal plastic bag and the overwrapped plastic bag). In some preferred embodiments, the dXCMSFH, dCMSFH, or dTBSFH of the present invention is stored in the absence of oxygen. The dXCMSFH, dCMSFH, or dTBSFH may be oxygenated prior to use such as, by way of example only, oxygenating before using in the catheter for cardiac therapy. In some embodiments, the dXCMSFH, dCMSFH, or dTBSFH can be stored in oxygen permeable or oxygen impermeable ("anoxic") containers in an oxygen controlled environment. Such oxygen controlled environments can include, for example, glove boxes, glove bags, incubators and the like. Preferably the oxygen content of the oxygen controlled environment is low relative to atmospheric oxygen concentrations (see, Kandler, R. L. et al., U.S. Pat. No. 5,352,773; herein incorporated by reference). In some embodiments of the present invention, the dXCMSFH, dCMSFH, or dTBSFH can be packaged in sealed Tyvek or Mylar (polyethylene terephthalate) bags or pouches. In some embodiments, the dXCMSFH, dCMSFH, or dTBSFH of the present invention can be lyophilized and stored as a powder. The preparations may be stored at room or elevated temperature (Kandler et al., PCT Publication No. WO 92/02239; Nho, PCT Publication No. WO 92/08478, both herein incorporated by reference), or more preferably under refrigeration. In some embodiments, the dCMSFH or dTBSFH may be stored in HyClone BioProcess Containers™ for ease of shipping and further handling.

Where the package is an oxygen impermeable film, the container can be manufactured from a variety of materials, including polymer films, (e.g., an essentially oxygen-impermeable polyester, ethylene vinyl alcohol (EVOH), or nylon), and laminates thereof. Where the container is an oxygen impermeable overwrap, the container can be manufactured from a variety of materials, including polymer films, (e.g., an essentially oxygen-impermeable polyester, ethylene vinyl alcohol (EVOH), or nylon) and laminates, such as a transparent laminate (e.g. a silicon oxide or EVOH containing-laminate) or a metal foil laminate (e.g., a silver or aluminum foil laminate). The polymer can be a variety of polymeric materials including, for example, a polyester layer (e.g., a 48 gauge polyester), nylon or a polyolefin layer, such as polyethylene, ethylene vinyl acetate, or polypropylene or copolymers thereof.

The containers can be of a variety of constructions, including vials, cylinders, boxes, etc. In a preferred embodiment, the container is in the form of a bag. A suitable bag can be formed by continuously bonding one or more (e.g., two) sheets at the perimeter(s) thereof to form a tightly closed, oxygen impermeable, construction having a fillable center. In the case of laminates comprising polyolefins, such as linear low density, low density, medium or high density polyethylene or polypropylene and copolymers thereof, the perimeter of the bag may be bonded or sealed using heat. It is well within the skill of the art to determine the shape of the bag and the appropriate temperature to generate a tightly closed, oxygen and/or moisture impermeable construction. Where the container is a film, such as a polyester film, the film can be rendered essentially oxygen-impermeable by a variety of suitable methods. The film can be laminated or otherwise treated to reduce or eliminate the oxygen permeability.

In some embodiments, one or more antioxidants, such as ascorbate (Wiesehahn, G. P. et al., U.S. Pat. No. 4,727,027; and, Kerwin, B. D. et al., U.S. Pat. No. 5,929,031), glutathione,N-acetylcysteine, methionine, tocopherol, butyl hydroxy toluene, butyl hydroxy anisole, or phenolic compounds (Osterber et al., PCT Publication No. WO 94/26286; and, Kerwin, B. D. et al., U.S. Pat. No. 5,929,031) may be added to further stabilize the dXCMSFH, dCMSFH, and dTBSFH (all references herein incorporated by reference).

Alternatively, and more preferably, the dXCMSFH of the present invention can be lyophilized and stored as a powder, or can be packaged in sealed Tyvek, or Mylar (polyethylene terephthalate) bags or pouches. Packaging such as, Kerwin, B. D. et al., U.S. Pat. No. 5,929,031, is herein incorporated by reference. In some embodiments, the dXCMSFH, dCMSFH, and dTBSFH in such storage containers may be subjected to irradiation or other sterilization treatment sufficient to extend the shelf-life of the compositions. An oxygen scavenger such as n-acetyl-cysteine may be included in the formulation.

The dXCMSFH, dCMSFH, and TBSFH of the present invention may be stored at suitable storage temperatures for periods of two years or more, and preferably for periods of two years or more, when stored in a low oxygen environment. Suitable storage temperatures for storage of one year or more are between about 0° C. and about 40° C. The preferred storage temperature range is between about 0° C. and about 25° C. The process of making dXCMSFH, dCMSFH, and dTBSFH of the present invention includes maintaining the steps of the process under conditions sufficient to minimize microbial growth, or bioburden, such as maintaining temperature at less than about 20° C. and above 0° C.

VI. Methods of Use

The deoxygenated stable NO-blocked tetrameric Hb of the present invention, and, in particular, the dXCMSFH may be used to form pharmaceutical compositions that may be administered to recipients, for example, by infusion, by intravenous or intra-arterial injection, or by other means. The dXCMSFH formulations of the present invention can be used in compositions useful as blood substitutes, volume expanders within the blood volume, and oxygen perfusion agents in any application where red blood cells are used. One application uses compositions of the present invention for the treatment of hemorrhage where blood volume is lost and both fluid volume and oxygen delivery capacity must be replaced. Moreover, because the deoxygenated stable NO-blocked tetrameric Hb of the present invention, and, in particular, dXCMSFH, can be made pharmaceutically acceptable, the formulations of the present invention can not only deliver oxygen but also act as simple volume expanders that provide oncotic pressure due to the presence of the large hemoglobin protein molecule. The deoxygenated stable NO-blocked tetrameric Hb of the present invention, and, in particular, dXCMSFH, can thus be used as replacement for blood that is removed during surgical procedures where the patient's blood is removed and saved for reinfusion at the end of surgery or during recovery (e.g., acute normovolemic hemodilution or hemoaugmentation, etc.).

A typical dose of the deoxygenated stable NO-blocked tetrameric Hb of the present invention, and, in particular, dXCMSFH as a blood substitute is from 10 mg to 7 grams or more of extracellular hemoglobin per kilogram of patient body weight. Thus, a typical dose for a human patient might be from a few grams to over 350 grams. It will be appreciated that the unit content of active ingredients contained in an individual dose of each dosage form need not in itself constitute an effective amount since the necessary effective amount could be reached by administration of a plurality of administrations as injections, etc. The selection of dosage depends upon the dosage form utilized, the condition being treated, and the particular purpose to be achieved according to the determination of the ordinarily skilled artisan in the field.

In some embodiments of the invention, a solution of a deoxygenated stable NO-blocked tetrameric Hb, for example, dXCMSFH, will contain about 5% to about 25% dXCMSFH by weight for administration to a mammal. In some preferred embodiments of the invention a solution of dXCMSFH will contain about 7% to about 15% dXCMSFH by weight for administration to a mammal. In some other preferred embodiments of the invention, a solution of dXCMSFH will be 10% by weight of dXCMSFH for administration to a mammal. In some embodiments of the invention, a dose to be administered to a mammal contains about 7 g of dXCMSFH. In some embodiments of the invention a dose to be administered to a mammal contains about 1 g of a deoxygenated stable NO-blocked tetrameric Hb, and in particular, dXCMSFH. In some embodiments of the invention, an exemplary unit of production for use in a therapeutic setting is a container with 500 ml of a 0.5 mmol solution of dXCMSFH (about 64 g/L, or about 6.4% by weight in solution). The larger unit solutions may be used for replacement of blood or for augmenting oxygen delivery for a number of therapeutic interventions. The smaller unit solutions may be used for labeling and diagnostic purposes, as well as therapeutic interventions. The smaller unit solutions may, in a preferred embodiment, contain a solution of dXCMSFH of up to 4%, 5%, 6%, 7%, 8%, 9%, 10%, 11%, 12%, 13%, 14%, 15%, 16%, 17%, 18%, 19%, 20%, 21, 22%, 23%, 24%, or up to 25% by weight of dXCMSFH. In another embodiment, a solution may contain dXCMFSH with a concentration as low as 2%, 3%, 4%, 5%, 6%, 7%, 8% 9%, 10%, 11%, 12%, 13% or 14%, by weight of dXCMSFH.

Administration of the deoxygenated stable NO-blocked tetrameric Hb of the present invention, and, in particular, dXCMSFH, can occur for a period of seconds to hours depending on the purpose of the hemoglobin usage. For example, as a volume augmentation therapy, the usual time course of administration is as rapid as possible. Typical infusion rates for hemoglobin solutions as oxygen delivery/perfusion agents or volume enhancers can be from about 100 ml to 3000 ml/h. However, when used to stimulate hematopoiesis, administration can be made more slowly and therefore administration rates can be slower because the dosage of the deoxygenated stable NO-blocked tetrameric Hb of the present invention, and, in particular, dXCMFSH may be much less than dosages that may be required to treat hemorrhage.

In some embodiments, the deoxygenated stable NO-blocked tetrameric Hb of the present invention, and, in particular, dXCMSFH, can be used to treat anemia as caused by renal failure, diabetes, AIDS, chemotherapy, radiation therapy, hepatitis, G.I. blood loss, iron deficiency, menorrhagia, and the like, by providing additional oxygen delivery capacity in a mammal that is suffering from anemia, as well as by stimulating hematopoiesis, providing an effective iron supplement to support RBC production, and by serving as an adjuvant to erythropoietin therapy.

Likewise, the deoxygenated stable NO-blocked tetrameric Hb of the present invention, and, in particular, dXCMSFH, can be used to provide additional oxygen delivery capacity to a mammal (such as an athlete, soldier, mountaineer, aviator, smoke victim, etc.) desiring such additional oxygen delivery capacity. Such additional oxygen delivery capacity can be used to overcome environmental (i.e, for example, high altitudes and smoke inhalation) and physical (i.e., for example, acute performance demands) stresses. The stable NO-blocked tetrameric Hbs of the present invention, and in particular, dXCMFSH, thus are useful in treating carbon monoxide poisoning and its concurrent hypoxia and ischemia, as the compounds and compositions of the present invention can supply oxygen to tissue while the carbon monoxide bound cellular hemoglobin is being eliminated, thus bridging the oxygen needs of the patient until new RBCs are produced.

The deoxygenated stable NO-blocked tetrameric Hbs of the present invention, and, in particular, dXCMSFH, can be used for applications requiring administration to a mammal of high volumes of hemoglobin as well as in situations where only a small volume of the hemoglobin of the present invention is administered. The deoxygenated stable NO-blocked tetrameric Hb of the present invention, and, in particular, dXCMSFH can be used in applications during surgery where large volumes of blood are normally lost, or in treatment of trauma victims who have lost large volumes of blood. This can include both civilian accidents and military situations.

The deoxygenated stable NO-blocked tetrameric Hb of the present invention, and, in particular, dXCMSFH may be used as a blood substitute in veterinary clinical applications.

In addition, because the distribution throughout the vasculature of the deoxygenated stable NO-blocked tetrameric Hb of the present invention, and, in particular, dXCMSFH, is not limited by viscosity or by the size of red blood cells, the compositions of the present invention can be used to deliver oxygen to areas that red blood cells cannot penetrate. These areas can include any tissue areas that are located downstream of obstructions to red blood cell flow, such as areas downstream of thrombi, sickle cell occlusions, arterial occlusions, angioplasty balloons, surgical instrumentation, tissues that are suffering from oxygen starvation or are hypoxic, and the like.

Additionally, all types of tissue ischemia, including ischemic events in the brain, can be treated using the methods of the instant invention. Such tissue ischemias include, for example, stroke, emerging stroke, transient ischemic attacks, myocardial stunning and hibernation, acute or unstable angina, emerging angina, infarct, and the like. The recovery of tissues from physical damage such as burns can also be accelerated by pretreatment with the hemoglobin of the present invention, which allows increased perfusion and oxygenation of the tissues which may also reduce infection risk. The use of the stable NO-blocked tetrameric Hbs of the present invention also will allow for better oxygen uptake in the lungs due to better distribution of these smaller molecules within small capillaries. In and after cosmetic surgery, fine tissue beds suffer microcirculatory disruption, thereby losing flow of RBCs. Use of the stable NO-blocked tetrameric Hbs of the present invention provide better oxygenation for tissue metabolism and regrowth, to decrease scarring with its loss of vascularization.

The deoxygenated stable NO-blocked tetrameric Hb of the present invention, and, in particular, dXCMSFH, can be used for the treatment of sickle cell anemia patients. Sickle cell anemia patients in vasoocclusive crisis are currently treated by transfusion of red blood cells in conjunction with dilution and pain management. The deoxygenated stable NO-blocked tetrameric Hb of the present invention, and, in particular, dXCMSFH, may not only deliver oxygen thereby preventing further sickling (as do red blood cells), they may also penetrate vessels already occluded with deformed red cells to better alleviate pain and minimize tissue damage. Also, frequent transfusions in the sickle cell anemia population may result in alloimmunization to red cells and to platelets, an adverse effect that would be avoided by use of hemoglobin of the present invention. The deoxygenated stable NO-blocked tetrameric Hb of the present invention, and, in particular, dXCMSFH, n offer a significant therapeutic advantage in treatment of sickle cell anemia patients, since they elicit a lesser degree of vasoconstriction or none at all. This is an advantage in the treatment of vasoocclusive crisis, and is also an advantage in other treatments of sickle cell anemia patients in situations where there is a risk of sudden onset of vasoocclusive crisis. For example, dXCMSFH of the present invention may be used in place of packed red cells for preoperative transfusion of sickle cell anemia patients to minimize risk of anesthesia. The deoxygenated stable NO-blocked tetrameric Hb of the present invention, and, in particular, dXCMSFH may also be administered periodically to minimize risk of stroke.

The stable NO-blocked Hb of the present invention, i.e, re-oxygenated XCMSFH can perfuse because of its size, and deliver oxygen to tissue beds that would normally be dependent upon diffusion alone due to the poor perfusion of bulky large red blood cells. For example, the compounds and compositions of the present invention can be used as a tissue protectant in acute coronary syndrome (ACS) and in transplantation, where the area of insult or harvested organ is perfused during stopped flow situations. This may prevent reperfusion injury and allow for the salvage and preservation of tissues that have been perfused, with subsequent normal circulation. Additionally, in transplantation procedures, organs may be prepared for harvesting by flushing with the compounds and compositions of the present invention to remove native blood agents and components prior to removal and continue to support tissue viability as discussed above.

The compounds and compositions of the present invention may also be utilized as a wound healing reagent where the molecular size and oxygen delivery capabilities may yield superior perfusion in poorly vascularized regions such as, for example, diabetic foot injuries, recovery from cardiac revascularization and post surgical recovery, i.e. for example, cosmetic surgery or cancer resection breast reconstruction, where RBCs may not perfuse well due to size or rigidity. Another application of the stable NO-blocked tetrameric Hbs of the present invention may be in poorly vascularized tumor tissue beds of cancer cells where appropriate use of the invention can allow for an increase in oxygen tension and allow for more effective use of radiation therapy and for the enhancement of oxygen dependent pharmaceutical agents.

The deoxygenated stable NO-blocked tetrameric Hb of the present invention, and, in particular, dXCMSFH, may be used as a small molecule inhibitor of nitric oxide for cardiogenic shock. Cardiogenic shock afflicts a significant number of patients presenting with acute myocardial infarction, whereby circulatory shutdown occurs after the infarct. Despite intervention with catheters or bypassgrafting, the mortality rate is about 50%. The use of the compounds and compositions of the present invention may provide the level of oxygenation to heart and blood vessels to forestall excessive production of nitric oxide and support survival past the critical initial thirty day post infarct time period. Survival is greatly enhanced after this timepoint.

The deoxygenated stable NO-blocked tetrameric Hb of the present invention, and, in particular, dXCMSFH contains iron, and as such, may be detected via MRI (magnetic resonance imaging). Thus, in some embodiments, the present invention contemplates the use of deoxygenated stable NO-blocked tetrameric Hb of the present invention, and, in particular, dXCMSFH as an imaging agent.

The present invention also concerns implantable delivery devices (such as cartridges, implants, etc.) that contain deoxygenated stable NO-blocked tetrameric Hb of the present invention, and, in particular, dXCMSFH, and that are capable of releasing dXCMSFH, for example, into the circulation in response to a sensed need for increased oxygen delivery capacity. In some embodiments, such devices can deliver dXCMSFH, for example, at a constant rate, so as to facilitate erythropoiesis (either alone, or in combination with erythropoietin). In some embodiments, the devices can be controlled by sensing means (such as electronic probes of hemoglobin, $O_2$ level, $CO_2$ level, etc.) so as to deliver the deoxygenated stable NO-blocked tetrameric Hb of the present invention at a rate commensurate with the patient's oxygen delivery capacity needs. Such sensing means may themselves be implantable, or part of the implanted device, or may be located extracorporeally. In some embodiments, such devices may be used to accomplish or facilitate the hemo-diagnosis of individuals.

The deoxygenated stable NO-blocked tetrameric Hb of the present invention, and, in particular, dXCMSFH may also be used to form non-pharmaceutical compositions that can be used, for example, as reference standards for analytical instrumentation needing such reference standards, reagent solutions, control of gas content of cell cultures; for example by in vitro delivery of oxygen to a cell culture, and removal of oxygen from solutions. Additionally, the dXCMSFH of the present invention may be used to oxygenate donated tissues and organs during transport.

The deoxygenated stable NO-blocked tetrameric Hb of the present invention, and, in particular, dXCMSFH may be used to scavenge endotoxin from surfaces or liquids. The invention thus contemplates devices, such as cartridges, filters, beads, columns, tubing, and the like that contain the deoxygenated stable NO-blocked tetrameric Hb of the present invention. Liquids, such as water, saline, culture medium, albumin solutions, etc., may be treated by passage over or through such devices in order to remove endotoxin that may be present in such liquids, or to lessen the concentration of endotoxin present in such liquids. The deoxygenated stable NO-blocked tetrameric Hb of such devices is preferably immobilized (as by affinity, ionic, or covalent bonding, etc.) to solid supports present in such devices. In some embodiments, the deoxygenated stable NO-blocked tetrameric Hb is bound to beads that may be added to the liquids being treated, and then subsequently removed (as by filtration, or affinity immobilization). In some embodiments, the beads may be of ferromagnetic or paramagnetic metal, or may be themselves magnetic, such that they may be readily separated from the treated liquid by magnetic means.

The deoxygenated thiol blocked Hb, both cross linked and uncross linked, i.e., dCMSFH, dTBSFH, and dXCMSFH, can be used to remove oxygen from solutions requiring the removal of oxygen, and as reference standards for analytical assays and instrumentation. The deoxygenated thiol blocked Hb, both cross linked and uncross linked, i.e., CMSFH, TBSFH, and XCMSFH, can also be used in vitro to enhance cell growth in cell culture by maintaining oxygen levels.

The re-oxygenated stable NO-blocked tetrameric Hb of the present invention, and in particular, XCMSFH, can be used for the use in visualizing intravascular space. Present optical techniques for the observation of vascular walls are relegated to non-optical techniques due to the opaque effects of the transfusion of red blood cells. The stable NO-blocked Hb of the present invention, i.e., XCMSFH may not only deliver oxygen thereby preventing ischemia, but they may also present an optically translucent field of view to allow for visualization of tissue beds in situ for the determination of pathology; cancer, vulnerable plaques, lipid damage, stent placement, etc, using visible light in the red wavelength band, for example, to illuminate the targeted feature. The use of Optical Coherence Tomography may be expanded by employing the stable NO-blocked tetrameric Hbs of the present invention. Intermittent saline flushes are currently employed to create transient visual fields in-vivo, but superior visualization and sustained examinations may be possible with use of the present stable NO-blocked tetrameric Hb, which can continue to oxygenate the local area.

VII. EXAMPLES

Example 1

Comparison of Two Methods of Initial Processing of Whole Blood

Materials: Bovine Blood Collection: Bovine blood is collected in a 1 gallon collection container which may hold 100 ml of 6% sodium ethylenediaminetetraacetic acid (EDTA) solution and is cooled in ice.

The whole bovine arterial blood is divided into Batch A and Batch B. Batch A consists of 2200 ml of whole blood and is washed in the haemonetics Cell Saver 5 to obtain concentrated red blood cells free of platelets, clotting factors, extra cellular potassium, anticoagulants, and cell stroma (Method A). Batch B consists of 1800 ml of whole blood and is washed on a Millipore 0.65 µm filter (Method B).

Method A. Cell Saver 5 removal of plasma proteins: Cell Saver 5 from Haemonetics is used to concentrate erythrocytes from other components in freshly collected anticoagulated bovine blood. It may be desirable not to fracture either leucocytes or erythrocytes at this point.

After being passed through a coarse filter of 150 µm, the cells are washed in a spinning bowl holding 225 ml of packed red blood cells and washed with 3 liters of saline in a reverse flow from the outside edge of the bowl towards the center. The centrifugation is gentle, and some of the WBCs are eluted in the wash, which may be desirable. Table 4 shows the progress of serum protein removal at 500 ml increments. It is a continuous flow technique. Sample in Table 4 is the sample volume applied to the bowl. Progress is followed by reading the protein concentration at 280 nm spectrophotometrically, with the values given in $A_{280}$ units (absorbance units at 290 nm). The data points in Table 4 are taken at the indicated points during the washing process. The results indicate that when a full bowl of red cells is washed with 3 liters of NS, there is a greater than 3 log reduction in serum proteins. This also infers a greater than 3 log reduction in viruses, prions, etc that are not bound to red cell membranes. All values in Table 4 are corrected for dilution.

TABLE 4

| Cell Saver 5 removal of plasma proteins | |
|---|---|
| Sample status | $A_{280}$ Absorbance Units |
| $A_{280}$ of initial crude plasma containing sample | 277.35 |
| $A_{280}$ of filtrate after 500 cc NS | 43.20 |
| $A_{280}$ of filtrate after 1000 cc NS | 7.69 |
| $A_{280}$ of filtrate after 1500 cc NS | 0.86 |
| $A_{280}$ of filtrate after 2000 cc NS | 0.05 |

Method B. Millipore 0.65 µm filter removal of plasma proteins: Batch B is passed through a 150 µm filter. The material is then filtered with a tangential flow membrane that will pass plasma proteins but retain cellular components such as leucocytes and erythrocytes. The tangential flow membrane filtration can be slower but it may require less labor as it can run unattended. It can be more suitable for scaleup. Other types of large scale centrifuges may be used. The results of this continuous diafiltration are shown in Table 5, where all results are corrected for dilution. This method reveals a greater than 3 log reduction in plasma proteins, which also implies a similar log reduction in viruses, prions, etc.

TABLE 5

Millipore 0.65 μm filter removal of plasma proteins

| Sample status | $A_{280}$ Absorbance Units |
|---|---|
| $A_{280}$ of plasma in 1000 cc blood | 221.6 |
| $A_{280}$ of filtrate after 1000 cc NS | 82.1 |
| $A_{280}$ of filtrate after 2000 cc NS | 26.5 |
| $A_{280}$ of filtrate after 3000 cc NS | 8.07 |
| $A_{280}$ of filtrate after 4000 cc NS | 2.76 |
| $A_{280}$ of filtrate after 5000 cc NS | 0.81 |
| $A_{280}$ of filtrate after 6000 cc NS | 0.29 |
| $A_{280}$ of filtrate after 7000 cc NS | 0.102 |

Evaluation of leucocyte loss/removal. It is desirable among the preparation of hemoglobin to remove any WBCs to remove granolocyte proteolytic enzymes from the hemoglobin solution. Thus at the stage of removing plasma proteins it is desirable to remove the WBCs without causing their lysis. The Cell Saver 5 technology can remove some of the WBCs in the floating buffy coat during centrifugation. However, the tangential flow membrane may retain all of the WBCs so an observed loss of WBCs may mean that cell lysis of the WBCs had occurred. Table 6 shows evaluation of the conservation of WBCs after filtration with Cell Saver 5 or Millipore 0.65 μm filter. When appropriately corrected for volume, both methods provide adequate protection from leucocyte lysis in the presence of RBCs.

TABLE 6

Evaluation of leucocyte loss/removal

| Sample | Initial WBC | Final WBC (Vol Adj) | % Recovery |
|---|---|---|---|
| Cell Saver 5 | $5.79 \times 10^3$ | $6.10 \times 10^3$ | 100% |
| Millipore 0.65 μm | $5.79 \times 10^3$ | $5.63 \times 10^3$ | 100% |

Batches A and B are then refrigerated for 8 h, whereupon both batches are passed through a Baxter leuko-reducing filter, which also removes viral materials. Batch A yields 1500 ml of RBCs while Batch B yields 1200 ml of RBCs. Samples are extracted from each batch throughout the course of cleaning.

Lysing Cells and Removing Stroma. The 1500 ml of RBCs from Batch A are diluted with 6000 ml of DI water. After allowing the cells 45 seconds to lyse, 750 ml of 9% N saline (NS) is added to the solution to minimize the lysing of any leukocytes present. The 1200 ml of RBCs from Batch B are lysed with 4800 ml of DI water. No saline is added to Batch B at this point. Next, both batches are passed over a 0.22 micron Pellicon filter. Once the hemoglobin has been filtered out and collected in a separate flask, it is passed over a second 10K Dalton Pellicon filter. This filters out any saline present which is discarded. The pure hemoglobin is recirculated into the original flask and is concentrated to a desired percentage, such as 13.5% (w/v).

Blocking Sulfhydryls of Hemoglobin with Iodoacetamide (IAM). After the samples are concentrated to 13.5% Hb, oxygen is removed as previously described, and the pH is adjusted to 7.4 with 0.1M sodium phosphate buffer. Oxygen remaining is <10 ppb. Two molar equivalents of IAM per mole of dSFH are added and the reaction is allowed to proceed for 1 h. Progress of the reaction is monitored by an iodide electrode. Unreacted IAM by ultrafiltration using PBS. Once iodide is removed the intermediate dCMSFH is stable and may be is packaged in oxygen barrier containers and can be safely stored at room temperature.

Deoxygenation and Cross-Linking: The stable intermediate product, dCMSFH, is again placed in an oxygen free (<10 ppm) environment and dissolved oxygen removed to a level of less than 0.010 ppm. Membrane contactor technology can be the method utilized to deoxygenate the hemoglobin in a controlled atmosphere with an oxygen level of less than 10 ppm. An initial oxygen saturation reading is taken for both batches using a polorgraphic dissolved oxygen probe. Batch A has an initial reading at 4 mg/L. Batch B has an initial reading at 7 mg/L. The hemoglobin is pumped and recirculated through the membrane contactor using a peristaltic pump at a flow rate of 600 ml/min with applied vacuum pressure of >28.5 in/Hg. The final oxygen saturation level for both batches is <0.01 ppm. The batches are then pH adjusted to 8.4 with 0.5M NaOH for cross-linking. Once the pH is adjusted, 2.94 g of bis-3,5-dibromosalicyl fumarate (DBSF) is added to Batch A (2 molar equivalents per sulfhydryl) while 1.47 g is added to Batch B (2 molar equivalents per sulfhydryl). Once cross-linking is complete, pH is adjusted with 0.5M citric acid back to 7.4 and the batches are stored in air-tight containers in the refrigerator.

The reaction is monitored by Capillary gel electrophoretic analysis is performed using a Beckman CoulterPA-800® Proteomics instrument with standard sample preparation, to determine the extent of cross-linking to monitor the reaction time course. The reaction is complete when 95% or more of the tetramer are cross-linked (data not shown). The samples are also evaluated in a Hemox Analyzer for the recording of blood oxygen equilibrium curves based on dual wavelength spectrophotometry.

Comparison of Method A and Method B Overall: The Method A and Method B purifications are run side by side to compare efficiency in releasing Hb while removing stroma and preventing leucocyte lysis. Either method will provide purified materials of acceptable quality, and both methods will provide purified materials of acceptable quality, and a combination of both methods may also be envisioned to be used in the methods of the invention.

Example 2

Lysing White Blood Cells

Determination of the relative time of lysing of WBCs is demonstrated. Preferential lysing of RBCs relative to WBCs allows optimization of red blood cell lysis to obtain the maximum amount of hemoglobin, without also introducing proteases from lysed WBCs.

Procedure: 2000 mls of whole blood is filtered through only the 100μ reservoir filter of the Cell Saver 5. Seven beakers are then filled with 200 mls of blood. One beaker is designated as the control. The other six beakers are then assigned a specific time for lysing at times of 30 seconds and then 1, 2, 3, 4, and 5 minutes. The control beaker is started and 910 mls of 0.9% saline solution is added. At time increments of 30 seconds, 1, 2, 3, 4, and 5 minutes a 10 ml sample is taken for white blood cell analysis.

For the remaining six beakers, 800 ml of DI water is added. After 30 seconds 110 ml of 9% saline is added to the first beaker to stop lysing. After being allowed to stir for approximately 30 seconds, a 10 ml sample is taken for white blood cell analysis. After 1 minute, 110 ml of 9% saline is then added to the second beaker. Again after being allowed to stir for 30 seconds, a 10 ml sample is taken. For the remaining four beakers, 110 ml of 9% saline is added at 2, 3, 4 and 5 minutes to stop lysing. After each time increment, a 10 ml sample is taken from each for white blood cell analysis via standard WBC quantitation.

Conclusion: As seen in FIG. 2, the lysing of the white blood cells can take place between 2 and 3 minutes. So in order to optimize red blood cell lysis, lysing can be stopped at two minutes. Due to the addition of DI water and saline, the volume is increased. The results shown in Table 7 are corrected for dilution.

TABLE 7

Determination of Relative Lysing Time of WBCs

| Time | Control (K/mm$^3$) (Control Beaker) | Experimental (K/mm$^3$) (Beakers 1-6) |
|---|---|---|
| 30 seconds | 5.9 | 5.2 |
| 1 minute | 5.4 | 4.9 |
| 2 minutes | 5.8 | 5.0 |
| 3 minutes | 7.4 | 4.5 |
| 4 minutes | 6.8 | 4.0 |
| 5 minutes | 5.7 | 3.4 |

Example 3

Rabbit Safety Trial

MATERIALS: Domestic rabbits are raised and treated by standard animal husbandry. IV access is established with a 22 or 24 gauge catheter into a shaven topically anesthetized ear vein for dXCMSFH infusion. IV infusion is metered with a syringe pump; the total volume usually given over 45-60 minutes. If blood is removed from rabbits, it is performed by inserting a 20-22 gauge catheter into the artery of the other ear. Procedures and infusions are done using a Velcro cloth wrap type restraint.

METHODS: Protocol A: Rabbits are prepared for infusion as above. dXCMSFH to be administered has a p50 for $O_2$ of 28-32 as determined on a TCS Hemox-Analyzer at 37° C. in pH 7.40 buffered NS, and is 12% w/v for the modified hemoglobin of the invention. The amount of dXCMSFH to be infused is based upon 10% of the estimated blood volume of a rabbit (56 ml/kg). This amount is placed into the syringe, and infused by the pump over 45-60 minutes. The IV catheter is then removed from the rabbit's ear and the rabbit returned to its cage for observation. The control rabbits receive Hb without the NO blockage chemical modification.

Protocol B: Venous and arterial access is prepared as above. A significant amount of rabbit blood, 54-75 cc, is removed from the arterial catheter while simultaneously an identical volume of dXCMSFH is infused through the venous access. This procedure is accomplished in 12-20 minutes total time. On subsequent days 2 and 3, 15 cc of dXCMSFH is infused through the heparin locked venous catheter over a 30 minute interval, twice each day with 4 h between infusions.

Results: Twenty-five (25) rabbits are infused according to protocol A, over an approximately 1 h period as shown in Table 8. All of these rabbits live beyond 72 h up to 75 days, without any deaths. Three (3) rabbits are infused with Hb without the NO blockage chemical modification. All of these rabbits die within 7-12 minutes of starting the infusion, as shown in Table 9. Four (4) rabbits receive large amounts of dXCMSFH, according to protocol B, as shown in Table 10.

All of these rabbits are alive and well for more than two weeks, without any subsequent deaths. The rabbits treated with dXCMSFH in either protocol A or B show 100% survival and no obvious signs of morbidity. Therefore, experimental subjects receiving 650-7500 mg/kg of XCMSFH tolerate the experimental protocols A and B well, while the treatment group receiving cell free Hb, with no further modifications, at levels of 125-160 mg/kg, expire upon first administration.

TABLE 8

| Rabbit ID | Weight (Kg) | Dose dXCMSFH (mg/Kg) | Outcome |
|---|---|---|---|
| 11 | 2.47 | 567 | survive |
| 15 | 2.4 | 583 | survive |
| 13 | 2.62 | 534 | survive |
| B7 | 2.36 | 636 | survive |
| CO | 2.52 | 476 | survive |
| B3 | 2.24 | 670 | survive |
| B1 | 2.8 | 714 | survive |
| C02 | 2.65 | 566 | survive |
| E03 | 2.38 | 630 | survive |
| 04 | 2.1 | 1143 | survive |
| 07 | 2.26 | 1062 | survive |
| C8 | 2.39 | 1004 | survive |
| MH2 | 3.12 | 808 | survive |
| LHD | 2.78 | 647 | survive |
| D03 | 2.3 | 783 | survive |
| D01 | 2.06 | 874 | survive |
| 05 | 2.29 | 629 | survive |
| 03 | 2.02 | 713 | survive |
| 01 | 2.12 | 679 | survive |
| JSD | 2.13 | 676 | survive |
| D04 | 2.26 | 637 | survive |
| MH4 | 2.51 | 574 | survive |
| K03 | 2.27 | 634 | survive |
| D08 | 2.28 | 632 | survive |
| D12 | 2.42 | 595 | survive |

TABLE 9

| Rabbit ID | Weight (Kg) | Elapsed time (min) | Dose dSFH (mg/Kg) | Outcome |
|---|---|---|---|---|
| 06 | 2.04 | 7 | 98 | expired |
| 10 | 2.39 | 12 | 126 | expired |
| 09 | 2.42 | 8 | 83 | expired |

TABLE 10

| Rabbit ID | Weight (Kg) | dXCMSFH (mg) | Dose dXCMSFH (mg/Kg) | Outcome |
|---|---|---|---|---|
| B03 | 3.1 | 12000 | 3871 | survive |
| F02 | 2.79 | 11500 | 4122 | survive |
| F01 | 3.02 | 13800 | 4570 | survive |
| F05 | 2.65 | 12700 | 4792 | survive |

Example 4

Pig Safety Trial

MATERIALS AND METHODS: Twelve piglets weighing 10-16 kilogram were studied. Prior to inclusion in the study, noninvasive screening by 2D echocardiogram for cardiac anomalies and aortic valve diameter measurements were performed. 5 mg of Lasix 40 mg/ml concentration was administered to each piglet immediately after establishing an IV, prior to initiating the top loading of the XCMSFH solution The XCMSFH solution had a p50 of 32 for Oxygen and a concentration of 12 gram percent (120 mg XCMSFH/ml). Each piglet received 1200 mg XCMSFH/kg body weight.

Non invasive cardiac data was obtained using a blood pressure cuff on a hind limb. Doppler ultrasound (USCOM) was used to measure the beat to beat cardiac output at various times throughout the infusion. The data selected for analysis represented the best ultrasound wave form obtained at any time point. Top loading the addition of study material was limited by the upper boundary of fluids producing congestive heart failure.

An amount equal to 14.3 percent of the calculated blood volume (70 ml blood/kg body weight) was infused through a peripheral IV over the course of one hour. Subject pigs were not anesthetized, sedated, or invasively monitored.

RESULTS: FIGS. 7A-D represent, in order, cardiac output, systemic vascular resistance, systolic blood pressure and diastolic blood pressure as a function of XCMSFH infused, corrected for body weight. All of the piglets tolerated the infusion well; there were no subject deaths. A least squares method of correlating variables was used to evaluate the data, providing slope and intercept. It is readily apparent that there is great variability in the data of any parameter, regardless of the amount of XCMSFH infused. This relates to the fact that the subjects were not sedated, nor restrained. Arousal, toileting, and handling seemed to account for most of the variation, though there was significant variation between subjects' parameters even before the initiation of any of the experiment.

The results of this study showed that the average (max, min) for these indices were: Cardiac Output, 1.12 L/min (2.7, 0.45); Systemic Vascular Resistance, 7008 dynes.sec/cm$^5$ (21590-3364); Systolic Blood Pressure, 156.69 mmHg (193-130); and Diastolic Blood Pressure, 95.75 mmHg (113-72); respectively. The baseline values for Cardiac Output were 1.26 L/min (1.62, 0.72); Systemic Vascular Resistance 9588 dynes.sec/cm$^5$ (12662-4991); Systolic Blood Pressure 140 mmHg (159-123); and Diastolic Blood Pressure, 84.25 mmHg (111-72); respectively. Cardiac output was observed to decrease slightly (<5%), while the systemic resistance increased by approximately 30%. Both systolic and diastolic blood pressure increased slightly (12 & 14%, respectively) during the infusion. The relationship between the varied dose overload of XCMSFH and the hemodynamic indices are represented in FIGS. 7A-D. Although, the effect of XCMSFH on these indices is minimal, this effect seems to be dependent on the % volume overload delivered.

In this study, significant variability was found for all parameters apparently independent of the amount of XCMSFH infused. The amount of minimal change in these cardiac parameters can be attributed to the increase in blood volume, essentially fluid overloaded subjects. Results of this study indicate that all subjects survived the experiment, and there were minimal changes in the cardiac parameters observed relating to vasoactivity.

PRION SAFETY: A number of measures are taken to ensure that the Hb of the invention are prion free. Selection of suitable animals is an initial step, choosing only animals from a closed herd, which have been fed no animal protein, given no antibiotics, and which are less than 30 months old. A second point for prevention of contamination is scrupulous attention to avoidance of mixing brain matter into blood. The sacrificial method of the "mushroom stunner" approach is chosen to eliminate the possibility of brain matter contamination, and thus eliminate potential introduction of prion containing materials into the collected blood. Further, when the Hb is processed, the washing procedure to remove plasma proteins will also remove prions. Additionally, when the Hb is filtered through the 300,00 Da molecular weight filter, any prions can be eliminated. Lastly, the Hb of the invention is processed through the Pall filter to remove leucocytes. At this point, small formed bodies such as prions and viruses can be removed. All of these precautions operate to secure the safety of the Hb of the invention for use in human therapeutics and emergency procedures.

Deoxygenated and Oxygenated States. The NO-blocked and stable NO-blocked tetrameric hemoglobins of the invention are packaged for storage and transport as deoxygenated species. For many therapeutic applications, the modified hemoglobins are used in the deoxygenated state. For applications where perfusion is required, for example, clearing a field of living tissue for observation, perfusing an ischemic region, or maintaining an organ ex-vivo prior to transplantation, the modified hemoglobins may be used in their re-oxygenated states to support tissue function.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of supplementing the blood of a mammal in need thereof, said method comprising administering to said mammal a composition comprising:
   a proteinaceous iron containing compound having a molecular weight of about 60,000 daltons to about 500,000 daltons and having at least one cysteine moiety wherein said cysteine moiety includes a thiol protecting group such that the proteinaceous compound is incapable of binding nitric oxide at the cysteine site, and wherein said compound is a cross-linked tetrameric hemoglobin, and
   a pharmaceutically acceptable carrier.

2. The method of claim 1 wherein said hemoglobin is non-pyrogenic, endotoxin free, oxygen free and stroma free.

3. The method of claim 1 wherein said hemoglobin has been cross linked with bis-3',5'-dibromo salicyl fumarate.

4. The method of claim 1 whereto said hemoglobin has been modified by reaction with pyridoxal-5'-phosphate.

5. The method of claim 1 wherein said hemoglobin is human hemoglobin.

6. The method of claim 1 whereto said hemoglobin is bovine or porcine hemoglobin.

7. The method of claim 1 wherein said thiol protecting group is selected from the group consisting of 4-pyridylmethyl, acetylaminomethyl, alkoxyalkyl, triphenylmethyl, carboxamidomethyl, acetyl, benzyl, benzoyl, tert butoxycarbonyl, p-hydroxyphenacyl, p-acetoxybenzyl, p-methoxybenzyl, 2,4-dinitrophenyl, isobutoxymethyl, tetrahydropyranyl, acetamidomethyl, benzamidomethyl, biscarboethoxyethyl, 2,2,2-trichloroethoxycarbonyl, tert-butoxycarbonyl, N-alkyl carbamate, and N-alkoxyalkyl carbamate.

8. The method of claim 1 wherein said thiol protecting group is a carboxamidomethyl group.

9. The method of claim 1 wherein said compound has increased oxygen delivery capacity compared to the oxygen carrying capacity of extracellular native human hemoglobin.

10. The method of claim 1 wherein said compound transports oxygen with a p50 of about 20 mm Hg to about 45 mm Hg.

11. The method of claim 1 wherein said administering is by an implant, injection or transfusion.

12. The method of claim 1 wherein said mammal suffers from anemia, anemia related conditions, hypoxia or ischemia.

13. The method of claim 1 wherein said mammal needs blood transfusion.

14. The method of claim 1 wherein said mammal is in trauma.

15. A method for treating a mammal in need of red blood cells by administering an effective amount of a proteinaceous iron containing compound which is a cross-linked tetrameric hemoglobin having a molecular weight of about 60,000 daltons to about 500,000 daltons and having at least one cysteine moiety wherein said cysteine moiety includes a thiol protecting group such that said proteinaceous compound has a reduced ability to bind nitric oxide at said cysteine site.

16. The method of claim 15 wherein said hemoglobin is non-pyrogenic, endotoxin free, oxygen free and stroma free.

17. The method of claim 15 wherein said hemoglobin has been cross linked with bis-3',5'-dibromo salicyl fumarate.

18. The method of claim 15 wherein said hemoglobin has been modified by reaction with pyridoxal-5'-phosphate.

19. The method of claim 15 wherein said hemoglobin is human hemoglobin.

20. The method of claim 15 wherein said hemoglobin is bovine or porcine hemoglobin.

21. The method of claim 15 wherein said thiol protecting group is selected from the group consisting of 4-pyridylmethyl, acetylaminomethyl, alkoxyalkyl, triphenylmethyl, carboxamidomethyl, acetyl, benzyl, benzoyl, tert butoxycarbonyl, p-hydroxyphenacyl, p-acetoxybenzyl, p-methoxybenzyl, 2,4-dinitrophenyl, isobutoxymethyl, tetrahydropyranyl, acetamidomethyl, benzamidomethyl, bis-carboethoxyethyl, 2,2,2-trichloroethoxycarbonyl, tert-butoxycarbonyl, N-alkyl carbamate, and N-alkoxyalkyl carbamate.

22. The method of claim 15 wherein said thiol protecting group is a carboxamidomethyl group.

23. The method of claim 15 wherein said compound has increased oxygen delivery capacity compared to the oxygen carrying capacity of extracellular native human hemoglobin.

24. The method of claim 15 wherein said compound transports oxygen with a p50 of about 20 mmHg to about 45 mm Hg.

25. The method of claim 15 wherein said administering is by an implant, injection or transfusion.

26. The method of claim 15 wherein said mammal in need of red blood cells suffers from a disorder is selected from the group consisting of anemia, anemia related conditions, hypoxia and ischemia.

27. The method of claim 26 wherein said anemia and anemia related conditions are caused by renal failure, diabetes, AIDS, chemotherapy, radiation therapy, hepatitis, G.I. blood loss, iron deficiency, or menorrhagia.

28. The method of claim 26 further comprising administering erythropoietin therapy to said mammal.

29. The method of claim 26 wherein said ischemia is caused by burns, stroke, emerging stroke, transient ischemic attacks, myocardial stunning and hibernation, acute angina, unstable angina, emerging angina, or infarct.

30. The method of claim 26 wherein said disorder is carbon monoxide poisoning.

31. The method of claim 26 wherein said disorder is recovery after surgery.

32. The method of claim 26 wherein said disorder is diabetic wound healing.

33. The method of claim 26 wherein said disorder is sickle cell anemia.

34. The method of claim 15 wherein said administering is prior to surgery.

35. The method of claim 26 wherein said disorder is acute coronary syndrome.

36. The method of claim 15 wherein said mammal needs blood transfusion.

37. The method of claim 15 wherein said mammal is suffering from trauma.

38. The method of claim 26 wherein said disorder is the lack of oxygen delivery capacity is caused by environmental stress or physical stress.

39. The method of claim 26 wherein said disorder is cardiogenic shock.

40. The method of claim 15 wherein said administering is performed in combination with radiation therapy.

41. The method of claim 15 further comprising administering to said mammal an oxygen dependent pharmaceutical agent.

42. The method of claim 15 wherein said administering to said mammal permits visualization of intravascular space in-vivo.

43. The method of claim 42 further comprising reoxygenating said proteinaceous iron containing compound prior to said administering to said mammal.

* * * * *